(12) United States Patent
Kubota et al.

(10) Patent No.: US 9,316,582 B2
(45) Date of Patent: Apr. 19, 2016

(54) INFORMATION ACQUIRING APPARATUS AND INFORMATION ACQUIRING METHOD OF ACQUIRING INFORMATION OF SAMPLE BY USING TERAHERTZ WAVE

(71) Applicant: CANON KABUSHIKI KAISHA, Tokyo (JP)

(72) Inventors: Oichi Kubota, Kawasaki (JP); Sayuri Yamaguchi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 33 days.

(21) Appl. No.: 14/225,038

(22) Filed: Mar. 25, 2014

(65) Prior Publication Data
US 2014/0291524 A1    Oct. 2, 2014

(30) Foreign Application Priority Data

Mar. 29, 2013 (JP) ................................. 2013-073649
Feb. 26, 2014 (JP) ................................. 2014-035844

(51) Int. Cl.
*G01N 21/55*    (2014.01)
*G01N 21/3586*    (2014.01)

(52) U.S. Cl.
CPC ................... *G01N 21/3586* (2013.01)

(58) Field of Classification Search
CPC ........................................ G01N 21/55
See application file for complete search history.

(56) References Cited

U.S. PATENT DOCUMENTS

| 7,326,930 B2 * | 2/2008 | Crawely ............... G01J 3/4338 250/341.1 |
| 2009/0231571 A1 * | 9/2009 | Itsuji ............................. 356/51 |
| 2011/0205528 A1 * | 8/2011 | Ogawa et al. ................... 356/51 |

FOREIGN PATENT DOCUMENTS

| CN | 101377406 A | 3/2009 |
| CN | 101769864 A | 7/2010 |

(Continued)

OTHER PUBLICATIONS

P.U. Jepsen et al.; "Investigation of Aqueous Alcohol and Sugar Solutions With Reflection Terahertz Time-Domain Spectroscopy;" Optics Express, vol. 15, No. 22, Oct. 29, 2007, pp. 14717-14737.

*Primary Examiner* — David Porta
*Assistant Examiner* — Faye Boosalis
(74) *Attorney, Agent, or Firm* — Canon USA, Inc. IP Division

(57) ABSTRACT

An information acquiring apparatus that acquires information of a sample includes an irradiation unit configured to irradiate an irradiation position of the sample with a terahertz wave through a transmission member being in contact with the sample; a detection unit configured to detect a terahertz wave reflected by the transmission member and a terahertz wave reflected by the sample; a waveform acquiring unit configured to acquire a time waveform of the terahertz wave reflected by the transmission member and a time waveform of the terahertz wave reflected by the sample, by using detection results of the detection unit; and an information acquiring unit configured to acquire the information of the sample by using the time waveform of the terahertz wave reflected by the transmission member, the time waveform of the terahertz wave reflected by the sample, and information relating to a thickness of the transmission member at the irradiation position.

19 Claims, 13 Drawing Sheets

(56) References Cited

FOREIGN PATENT DOCUMENTS

| CN | 101975754 A | 2/2011 |
| CN | 102004080 A | 4/2011 |
| CN | 102621083 A | 8/2012 |
| CN | 102667442 A | 9/2012 |
| JP | 4046158 B2 | 2/2008 |
| JP | 2011-112548 A | 6/2011 |
| JP | 2012-237657 A | 12/2012 |

\* cited by examiner

INFORMATION ACQUIRING APPARATUS AND INFORMATION ACQUIRING METHOD OF ACQUIRING INFORMATION OF SAMPLE BY USING TERAHERTZ WAVE

BACKGROUND OF THE INVENTION

1. Field of the Invention

One disclosed aspect of the embodiments relates to an information acquiring apparatus and an information acquiring method of acquiring information of a sample by using a terahertz wave.

2. Description of the Related Art

In recent years, various inspection technologies using electromagnetic waves with frequencies in a range from 30 GHz to 30 THz, so-called terahertz waves, have been developed. Japanese Patent No. 4046158 describes a measurement method for executing a nondestructive inspection by using transmissivity of a terahertz wave. This method irradiates a sample with an ultra-short pulse of a terahertz wave, detects a reflected wave from the sample to obtain a time waveform, and checks the configuration and state of each layer of the sample from the time waveform.

As indicated by P. U. Jepsen et al., Optics Letters, (2007), 15, 14717, a peak waveform of a time waveform may be checked in detail, and a complex refractive index spectrum at a position near an interface corresponding to a peak waveform may be obtained. It is known that many materials have specific absorption in a frequency band of terahertz waves, providing expectations for a new method of material analysis. Also, Japanese Patent Laid-Open No. 2011-112548 discloses a technology that measures a refractive index distribution of a front surface of a living body sample for a terahertz wave, and visualizes the result. Such an inspection technology using a terahertz wave provides expectations for application to medical use, such as pathologic diagnosis using a phenomenon in which the refractive index and reflectivity of a living tissue vary depending on a portion and a state (normal cell or tumor cell).

In measurement with a reflection system, a terahertz wave reflected by a mirror is measured in addition to a terahertz wave reflected by a sample, and acquires information of the sample by using time waveforms of the terahertz waves. However, if the positions of the front surface of the sample and the front surface of the mirror are not the same, or if the intensity of a terahertz wave varies every measurement, correct comparison cannot be made, and hence measurement accuracy may be decreased. To address this, a method for measurement by using a plate-shaped transmission member that transmits a terahertz wave is used. This is a method of irradiating a sample with a terahertz wave through a transmission member while the transmission member contacts the sample.

In the past, various types of measurement have been executed based on an assumption that the transmission member has a uniform thickness in plane. However, it is difficult to manufacture a transmission member with a uniform thickness in plane. The expected thickness may differ from the thickness at an actually measured position, or the thickness of the transmission member may vary every irradiation position of the terahertz wave. Hence, it is difficult to constantly satisfy accuracy which is currently expected.

SUMMARY OF THE INVENTION

According to an aspect of the embodiments, an information acquiring apparatus that acquires information of a sample includes an irradiation unit configured to irradiate an irradiation position of the sample with a terahertz wave through a transmission member being in contact with the sample; a detection unit configured to detect a terahertz wave reflected by the transmission member and a terahertz wave reflected by the sample; a waveform acquiring unit configured to acquire a time waveform of the terahertz wave reflected by the transmission member and a time waveform of the terahertz wave reflected by the sample, by using detection results of the detection unit; and an information acquiring unit configured to acquire the information of the sample by using the time waveform of the terahertz wave reflected by the transmission member, the time waveform of the terahertz wave reflected by the sample, and information relating to a thickness of the transmission member at the irradiation position.

Further features of the disclosure will become apparent from the following description of exemplary embodiments with reference to the attached drawings.

DESCRIPTION OF THE EMBODIMENTS

Figure 1:
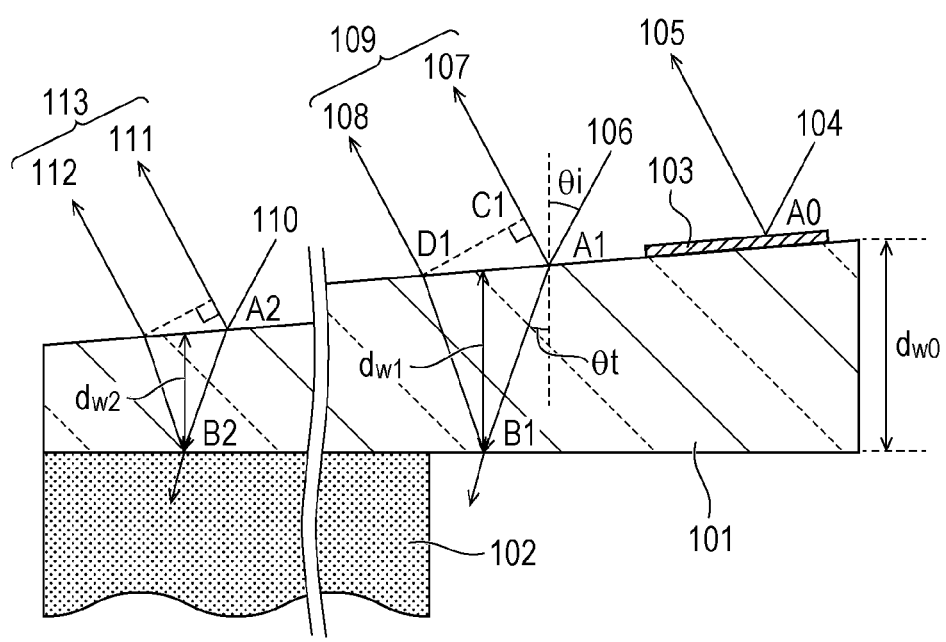
FIG. 1 is an illustration explaining a path of a terahertz wave during measurement according to an embodiment.

An embodiment of the disclosure is described below with reference to the drawings.

In this embodiment, a transmission member that transmits a terahertz wave well is brought into contact with a sample, and then the sample is irradiated with a terahertz wave through the transmission member. The transmission member is a plate-shaped member with a known complex refractive index. The transmission member is brought into contact with a sample to planarize the sample, and standardizes a variation in intensity of a terahertz wave from a time waveform of a terahertz wave reflected by the front surface of the transmission member. An information acquiring apparatus according to this embodiment detects a terahertz wave reflected by the front surface of the transmission member and a terahertz wave reflected by the front surface of the sample, and acquires time waveforms by time-domain spectroscopy (TDS). By analyzing the acquired time waveforms, information of the sample including the property of the sample, such as a reflectivity and a complex refractive index spectrum, and the shape etc. of the sample can be acquired. To be specific, a time waveform corresponding to a reflected wave from the front surface of the transmission member and a time waveform corresponding to a reflected wave from the front surface of the sample (the interface between the back surface of the transmission member and the sample) are used. In this specification, "the front surface of the transmission member" is defined as a surface that the terahertz wave emitted from an irradiation unit reaches first. The opposite surface is defined as "the back surface of the transmission member."

Also, in this specification, "the information of the sample" is defined to include at least one of "the property" and "the shape" of the sample. To be specific, "the property" of the sample is defined to include the complex amplitude reflectivity, complex refractive index, complex dielectric constant, reflectivity, refractive index, absorption coefficient, dielectric constant, and electrical conductivity of the sample.

Also, "the shape" of the sample is defined to include the outside shape of the sample, the shape of a substance in the sample, the shape of a region including a predetermined property in the sample, and the thickness of a layer in the sample. The shape of the substance in the sample and the thickness of the layer in the sample can be acquired by using the difference between a time, at which a time waveform of a terahertz wave reflected by the interface, where the property is changed in the sample, is detected, and a time, at which a time waveform of a terahertz wave reflected by the transmission member or another interface is detected. Also, the shape of the region having the predetermined property in the sample is the shape of a region where property values of the sample are the same or in a predetermined range. For example, when the complex refractive index is acquired as the property of the sample, the shape of the region having the predetermined property can be acquired if a display method is changed such that the region where the complex refractive index is the predetermined value is indicated with blue and the other region is indicated with red. The type of information of the sample can be properly selected by a user.

The transmission member used for measurement desirably has a front surface and a back surface being flat, being parallel to each other, and has a uniform thickness in plane. To acquire the information relating to the property or shape of the sample, it is required to correctly recognize the influence, which is generated when a terahertz wave passes through the transmission member, because the influence varies depending on the thickness of the transmission member. However, it is difficult to constantly satisfy accuracy which is currently expected, by a measurement method of related art. Hence, a technology that can acquire the information of the sample with high accuracy is requested even if a transmission member not having a uniform thickness in plane is used. Also, a technology that can acquire the information of the sample with high accuracy is requested even if the thickness of each of transmission members is different.

In this embodiment, information relating to the thickness of the transmission member at the irradiation position is acquired, and used for acquiring the information of the sample. Accordingly, even if the thickness of the transmission member used for measurement is not uniform, the measurement result with high accuracy can be acquired.

FIG. 1 is a cross-sectional view showing the positional relationship among a transmission member, a sample, and a terahertz wave during measurement. The overview of the embodiment is described with reference to FIG. 1.

Reference sign 101 denotes a transmission member for measurement, to arrange a sample. The material of the transmission member may be desirably a known material that transmits a terahertz wave well and has a stable characteristic. Also, the material may desirably have a certain hardness. To be specific, the material may be a quartz substrate, a single crystal Si plate, etc. The complex refractive index spectrum can be easily measured by, for example, terahertz time-domain spectrometry with a transmission system.

The back surface of the transmission member 101 contacts a sample 102. At this time, the transmission member 101 may be in close contact with the sample 102 without a gap.

Also, a mirror 103 may be provided on a portion of the front surface of the transmission member 101. The mirror 103 is formed of a metal thin film by a method of vapor deposition or the like. The mirror 103 is used for obtaining reference light. The detail will be described later. Also, the mirror 103 is used as a marker when the obtained measurement result is compared with a measurement result obtained from the actual sample 102 or by a different measurement method, to cause the positions of these measurement results to correspond to each other.

The measurement for the complex refractive index of the sample 102 is described here for an example; however, the disclosure is not limited thereto.

The sample 102 is properly arranged in the apparatus, then a position A0 on the mirror 103 is irradiated with an incident wave 104 ($E_{i0}$) of a terahertz wave pulse, and a reflected wave 105 ($E_{o0}$) is measured. The reflected wave 105 ($E_{o0}$) represents the incident wave 104 ($E_{i0}$) well, and hence is a reference wave for previously knowing the waveform of a generated terahertz wave. Also, as described above, the reflected wave 105 ($E_{o0}$) may be used as a marker for recognizing the irradiation position. The measurement of the reference wave may not be occasionally required depending on the apparatus configuration etc., and hence may be executed only when an operator determines that the measurement is required.

A position A1 in a region, where the sample 102 is not arranged on the back surface of the transmission member 101 and only the transmission member 101 is provided, is irradiated with an incident wave 106 ($E_{i1}$) of the terahertz wave pulse, and a reflected wave 109 ($E_{o1}$) is measured. The reflected wave 109 includes a reflected wave 107 ($E_{o11}$) from the front surface of the transmission member 101, a reflected wave 108 ($E_{o12}$) reflected once by the back surface of the transmission member 101 and returned, and a reflected wave group reflected at least two times by the back surface of the transmission member 101 (not shown, but in a similar manner) and returned. It is assumed that the data obtained by measuring the region provided only with the transmission member 101 is reference data.

The reference data is used for checking the influence given to the terahertz wave when the terahertz wave makes a round trip in the transmission member 101. Hence, the reference data is not limited to the time waveforms of the reflected wave 107 and the reflected wave 108, but may include the thickness of the transmission member 101 at a position B1, or a frequency spectrum that is obtained by executing Fourier transform on the obtained time waveforms.

Also, the reference data may be data that is obtained by measuring a member having complex refractive index approximately equal to that of the transmission member 101 used for the measurement. Also, only the transmission member 101 may be solely measured and reference data may be acquired, before the transmission member 101 is brought into contact with the sample 102.

At the irradiation spot A1, the incident wave 106 is incident on the front surface of the transmission member 101 at an angle of incidence $\theta_i$, and propagates in the transmission member at an angle of refraction $\theta_r$. The thickness of the transmission member 101 at the irradiation spot A1 is $d_{w1}$. In FIG. 1, the reflected wave 107 ($E_{o11}$) propagates from A1 to C1 in the air, and the reflected wave 108 ($E_{o12}$) propagates from A1 to B1, and then to D1 in the transmission member 101. Hence, a phase difference is generated between the reflected waves 107 ($E_{o11}$) and 108 ($E_{o12}$). The phase difference appears as a time difference in the time waveforms. It is assumed that the time difference is $\Delta t_{A1}$. The time difference $\Delta t_{A1}$ depends on the angle of incidence $\theta_i$, the thickness $d_{w1}$ of the transmission member 101, and a refractive index $n_w$ of the transmission member 101, and is given by Expression (1) as follows.

$$\Delta t_{A1} = \frac{2 n_w d_{w1}}{c} \cdot \sqrt{1 - \frac{\sin^2 \theta_i}{n_w^2}} \quad (1)$$

With Expression (1), a thickness $d_w$ of the transmission member 101 at an irradiation spot is expressed by Expression (2). It is to be noted that $\Delta t$ is a time difference between two time waveforms corresponding to reflected waves from the front surface and back surface of the transmission member 101. With Expression (2), the thickness $d_{w1}$ of the transmission member 101 at the irradiation spot A1 can be obtained from the time difference $\Delta t_{A1}$.

$$d_w = \frac{c \Delta t}{2 n_w \cdot \sqrt{1 - \frac{\sin^2 \theta_i}{n_w^2}}} \quad (2)$$

Then, a spot in a region, where the sample 102 contacts the back surface of the transmission member 101, for example, A2 is irradiated with a terahertz wave 110 ($E_{i2}$), and a reflected wave 113 ($E_{o2}$) is measured. A portion provided by a reflected wave 111 ($E_{o21}$) and a portion provided by a reflected wave 112 ($E_{o22}$) are extracted from the time waveform, and a complex amplitude reflectivity $r\sim_{wsB2}$ at a position near an irradiation spot B2 (hereinafter, occasionally called irradiation position) from the transmission member 101 to the sample 102 is obtained. In this specification, "r~" in the expression and "n~" in expressions (described later) represent complex numbers.

At this time, by using the measurement result of the reflected wave 109, the influence generated when the measurement is executed through the transmission member 101 is eliminated. To be specific, the influence may include the phase difference between the reflected wave 111 ($E_{o21}$) and the reflected wave 112 ($E_{o22}$) generated when the reflected wave 112 ($E_{o22}$) makes a round trip in the transmission member 101 with a thickness of $d_{w2}$, and a deviation between a position at which the reflected wave 111 is incident on a detection unit and a position at which the reflected wave 112 is incident on the detection unit. Therefore, a ratio is obtained for each frequency, like Expression (3).

$$\tilde{r}_{ws\_B2}(\omega) = \tilde{r}_{wa} \cdot \left( \frac{F[E_{o22}]}{F[E_{o21}]} \middle/ \frac{F[E_{o12}]}{F[E_{o11}]} \right) \cdot \Delta d_w(d_{w1}, d_{w2}) \quad (3)$$

$r\sim_{wa}$ in the right side is a complex amplitude reflectivity from the transmission member 101 to the air, and is given by Expression (4) with use of a complex refractive index $n\sim_w$ of the transmission member 101.

$$\tilde{r}_{wa}(\omega) = (\tilde{n}_w - 1)/(\tilde{n}_w + 1) \quad (4)$$

F[E*] represents Fourier transform of a time waveform E*. For example, F[$E_{o22}$] is a signal obtained by executing Fourier transform on the time waveform $E_{o22}$ of the reflected wave from the back surface of the transmission member 101, extracted from the reflected wave 113.

Also, $\Delta d_w(d_{w1}, d_{w2})$ is a term for correcting a phase shift for a round trip, provided by the difference between the thickness of the transmission member 101 at the irradiation spot A1 and the thickness of the transmission member 101 at the irradiation spot A2. The term is expressed by Expression (5).

$$\Delta d_w(d_{w1}, d_{w2}) = \exp\left( -2i \cdot \frac{n_w \omega}{c} \cdot (d_{w1} - d_{w2}) \sqrt{1 - \frac{\sin^2 \theta_i}{n_w^2}} \right) \quad (5)$$

A complex refractive index $n\sim_s$ of the sample 102 is obtained from the complex amplitude reflectivity $r\sim_{ws}$ from the transmission member 101 to the sample 102 and the complex refractive index $n\sim_w$ of the transmission member 101, which are obtained as described above.

$$\tilde{n}_s(\omega) = \tilde{n}_w \cdot (1 - \tilde{r}_{ws})/(1 + \tilde{r}_{ws}) \quad (6)$$

The obtained complex refractive index $n\sim_s$ may be output as the information of the sample 102, or the shape of a region of a predetermined value or in a predetermined range in the complex refractive index $n\sim_s$ acquired at each irradiation position may be obtained. Also, if the refractive index of a substance included in the sample 102 or a desirable layer in the sample 102 is known, the position of the substance or layer can be recognized as the information of the sample 102, and the shape of the substance and the thickness of the layer in the sample 102 can be acquired. To be specific, the time difference between a time, at which a time waveform of a terahertz wave pulse reflected by the interface in the sample 102 is detected, and a time, at which a time waveform of a terahertz wave pulse reflected by the front surface of the transmission member 101 is detected, is obtained, and then the position of the interface can be obtained by using Expression (2). At this time, if the thickness of the transmission member 101 is different, the position of the interface cannot be correctly obtained. Hence, a thickness error in plane of the transmission member 101 may be corrected by using the above-described method.

When the complex refractive index $\tilde{n}_s$ of the sample 102 is obtained, the accuracy of the difference in thickness of the transmission member 101 ($d_{w1}-d_{w2}$) is important. That is, when the complex refractive index $\tilde{n}_s$ of the sample 102 is obtained, by increasing the accuracy of the difference in thickness of the transmission member 101, a phase shift $\Delta d_w$ at high-frequency side is restricted, and the influence on the spectrum to be calculated can be decreased.

In this embodiment, as described above, the data only about the transmission member 101 is used as the reference data when the information of the sample 102 is obtained. On the basis of the thickness of the transmission member 101 obtained from the reference data, correction regarding the difference with respect to the thickness of the transmission member 101 at another irradiation position is executed for each irradiation position. Accordingly, the information of the sample 102 can be accurately obtained. To be specific, the information of the sample 102 is acquired by using the time waveform acquired by measurement and information relating to the thickness of the transmission member 101 at the irradiation position. In this specification, "the information relating to the thickness of the transmission member at the irradiation position" is defined to include the thickness of the transmission member 101 at the irradiation position, the difference between the thickness of the transmission member 101 obtained from the reference data and the thickness of the transmission member 101 at the irradiation position, and the time difference between the time, at which the terahertz wave reflected by the front surface of the transmission member 101 is detected, and the time, at which the terahertz wave reflected by the sample 102 is detected, in the time waveform.

The information acquiring apparatus according to this embodiment can measure a portion (the front surface etc. of skin or viscus) of a living body, such as an animal or a human, in a state in which the body is living (in-vivo). Hence, in this specification, "the sample" is defined to include not only an object such as a living body sample, but also (a portion of) a living body.

EXAMPLE 1

Next, Example 1 is described in detail with reference to the drawings.

In this example, measurement is executed at a plurality of spots while the irradiation position of the terahertz wave is properly changed. Refractive indices in a 10-mm-long and 12-mm-wide region of the front surface of the sample are obtained, and the plane distribution of the refractive indices is created.

A representative apparatus configuration and a sample configuration are described, and then a waveform to be measured, a processing procedure for the measurement, and an effect of the measurement are described.

Figure 2:
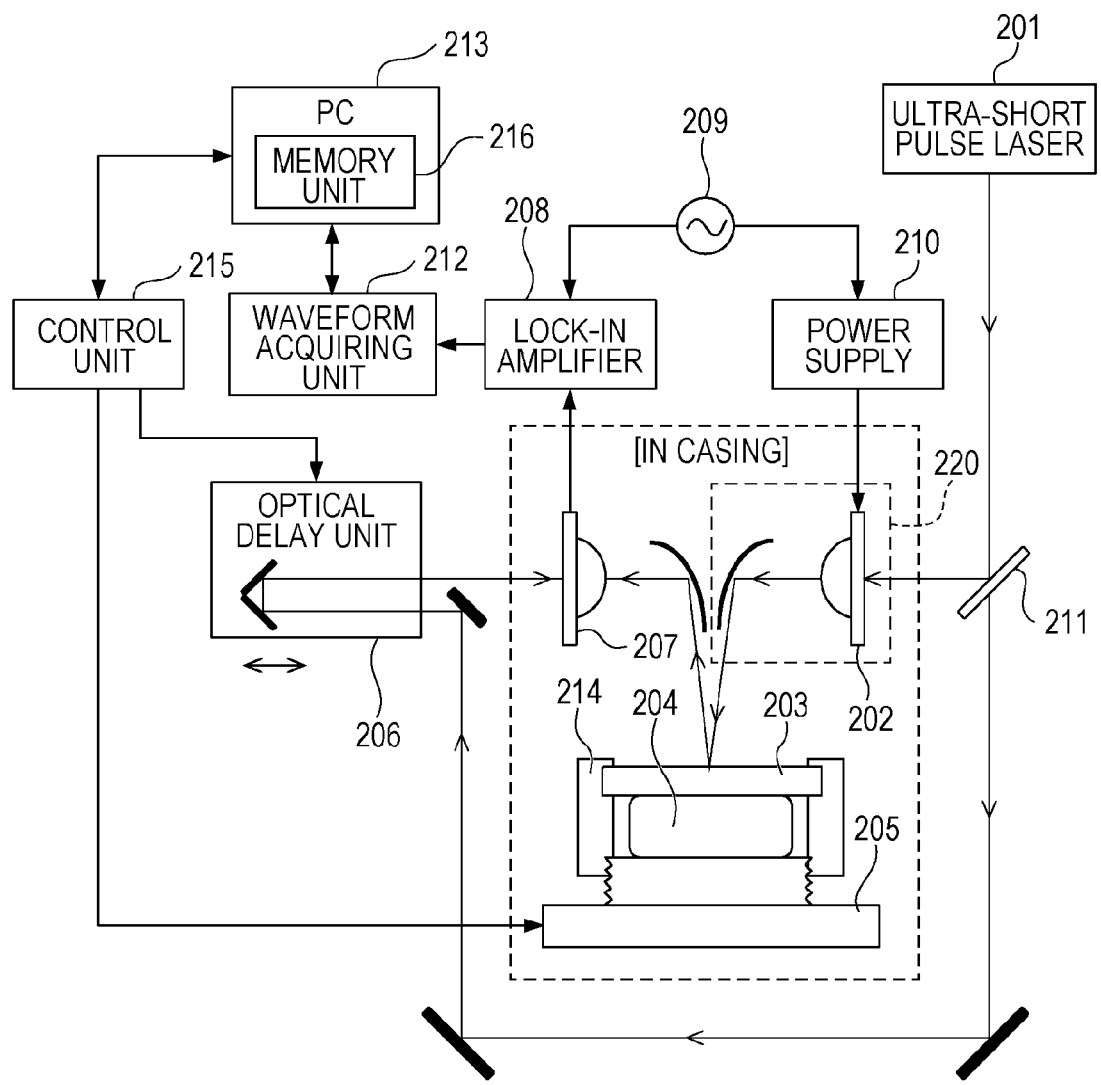
FIG. 2 is an illustration explaining a configuration of an information acquiring apparatus according to Example 1.

FIG. 2 shows an example of an information acquiring apparatus according to this example.

The information acquiring apparatus in this example includes an ultra-short pulse laser 201, a half mirror 211, an irradiation unit 220, a sample stage 205, an optical delay unit 206, a detection unit 207, a lock-in amplifier 208, a waveform acquiring unit 212, a control unit 215, a personal computer (PC) 213, and a sample holder 214.

First, the irradiation unit 220 of the information acquiring apparatus is described. The irradiation unit 220 in this example includes a generation photoconductive element (generation unit) 202, and an optical system that guides a generated terahertz wave pulse to a sample 204. When light generated by the ultra-short pulse laser 201 and passing the half mirror 211 is incident on the generation unit 202, a terahertz wave pulse is generated and is guided to the sample 204 through the optical system.

The ultra-short pulse laser 201 outputs ultra-short pulse laser light in the order of femtosecond. The output ultra-short pulse laser light is branched by the half mirror 211. One portion of the branched ultra-short pulse laser light is emitted on the generation photoconductive element 202. The other portion of the ultra-short pulse laser light passes through the optical delay unit 206 (described later), and is emitted on the detection photoconductive element (detection unit) 207. When the ultra-short pulse laser light is emitted on the generation photoconductive element 202, a terahertz wave pulse is generated. The intensity of the terahertz wave pulse is substantially proportional to a bias voltage that is applied by a power supply 210.

The terahertz wave pulse obtained from the front surface of the photoconductive element 202 is collected, and then is emitted on the sample 204 through a transmission member (hereinafter, called "window") 203. The window 203 is a flat plate-shaped member that transmits a terahertz wave well, which is described later in detail.

Next, the detection unit 207 is described. The detection unit 207 in this example is a detection photoconductive element.

The detection unit 207 detects the electric field strength of the terahertz wave pulse. The terahertz wave pulse reflected by the front surface of the window 203, the front surface of the sample 204 (the back surface of the window 203), etc., is collected by the optical system that guides the terahertz wave pulse to the detection unit 207, and is incident on the front surface of the detection unit 207.

In contrast, the ultra-short pulse laser light branched by the half mirror 211 and guided to the optical delay unit 206 as an adjustment unit passes through the optical delay unit 206 and is incident on the back surface of the detection unit 207. The optical delay unit 206 is an adjustment unit that adjusts the time point at which the terahertz wave is detected by adjusting the optical path length of the ultra-short pulse laser light. The detection unit 207 outputs current, which is proportional to the amplitude intensity of the incident terahertz wave pulse only for a period in which the ultra-short pulse laser light is incident on the back surface. The control unit 215 controls the detection time point of the terahertz wave pulse by controlling the optical delay unit 206 and changing the optical path length of the ultra-short pulse laser light.

Then, the lock-in amplifier 208 executes phase-sensitive detection on the signal detected by the photoconductive element 207, and sends an output signal to the waveform acquiring unit 212.

An oscillator 209 is connected to the power supply 210 and the lock-in amplifier 208. The oscillator 209 has a function of modulating a bias voltage of the photoconductive element 202, and a function of supplying a periodic signal to the power supply 210 and the lock-in amplifier 208.

The optical system of the terahertz wave (including a space for sending/receiving a terahertz wave and a space for propagation of a terahertz wave) is stored in a casing (indicated by a dotted line in FIG. 2) filled with the dry air or nitrogen, to prevent the terahertz wave from being absorbed by water vapor during measurement.

The waveform acquiring unit 212 captures an output signal, which is the detection result of the detection unit 207 from the lock-in amplifier 208, and obtains the time waveform of the terahertz wave pulse reflected by the sample 204.

The control unit 215 controls the optical delay unit 206. Also, the control unit 215 controls the sample stage 205, which is a position change unit that changes the irradiation position. In this example, the sample holder 214 can be mounted to and removed from the sample stage 205. For measurement, the window 203 and the sample 204 are held at the sample holder 214, and then the sample holder 214 is fixed to the sample stage 205. The sample stage 205 is a position change unit that freely moves the sample holder 214 and the sample 204 based on the signal from the control unit 215, and hence changes the irradiation position of the terahertz wave pulse.

The computer (PC) 213 is connected to the waveform acquiring unit 212 and the control unit 215. The PC 213 serves as an interface with respect to an operator, for example, by setting a measurement condition or displaying a result. Also, the PC 213 is an information acquiring unit that analyzes a series of time waveforms obtained by measurement, according to a procedure (described later) based on the above-described principle, and acquires information of the sample 204. The PC 213 includes a memory unit 216 that manages and stores data of a complex refractive index spectrum of the window 203, and data of a series of distribution measurement.

In this example, the control unit 215 and the PC 213 are separately provided. However, the function of the control unit 215 and the function of the PC 213 may be provided by a single computer or the like. Also, the function of the waveform acquiring unit 212 and the function of the PC 213 may be provided by a single computer or the like. The information of the sample 204 acquired by the information acquiring apparatus according to this example is displayed on a display (not shown) of, for example, a PC, in the form of frequency spectrum or front surface distribution.

Figure 3A:
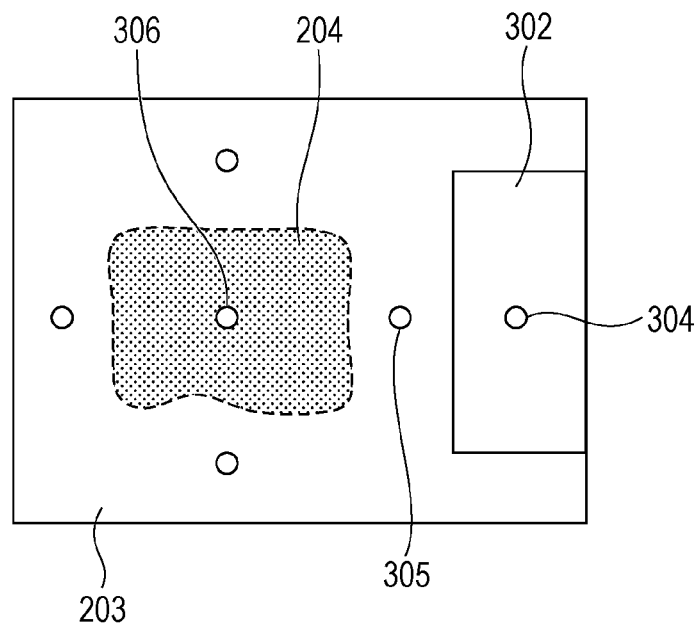
FIG. 3A is an illustration explaining arrangement of a sample and a transmission member according to Example 1.
Figure 3B:
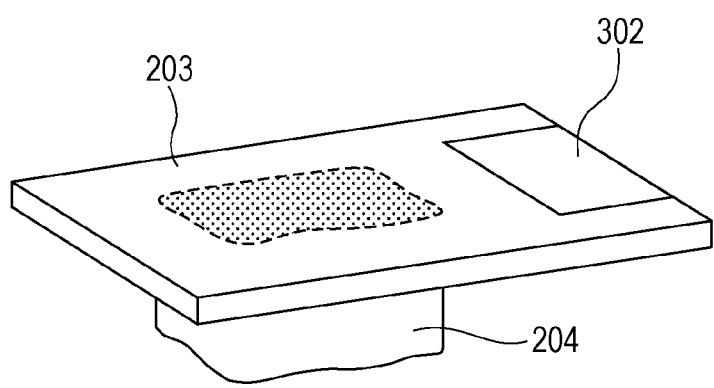
FIG. 3B is a perspective view explaining the arrangement of the sample and the transmission member according to Example 1.

FIGS. 3A and 3B show an example of a sample configuration during measurement. FIG. 3A is an illustration of the window 203 viewed from the front surface. FIG. 3B is a perspective view of the window 203 and the sample 204.

The window 203 serving as the transmission member of this example is a single crystal quartz plate of z-cut. The window 203 has a thickness of about 1 mm. The front surface and the back surface of the window 203 are processed to be flat. The window 203 has a surface roughness Ra of 0.1 μm or smaller, or more preferably, 1 nm or smaller. The quartz plate has features suitable for a window for measurement. That is, the hardness is sufficient, unnecessary scattering does not appear at the front surface, and absorption in a terahertz band is relatively small. Also, the refractive index is almost constant, and the optical anisotropy is small if a crystal is cut in a direction perpendicular to the optical axis (z-cut).

A gold thin film is provided on a portion of the front surface of the window 203 by vapor deposition, and thus, a mirror surface 302 is formed. The area of the mirror surface 302 is largely provided so that the area is sufficiently larger than the size of the beam spot of the terahertz wave pulse. The area desirably has a length and a width, each of which is at least 5 times the diameter of the spot. This is because a component of a low-frequency band is spread even outside the beam spot although the component is weak.

In contrast, the front surface (surface to be measured) of the sample 204 is finished to be flat, and is formed to contact with the back surface of the window 203. If a gap due to an air bubble or the like is present at a position near the irradiation spot, a complex refractive index to be calculated is the value of the gap (the air), and in many cases, the value is deviated from the value of the complex refractive index at the front surface of the sample 204. Owing to this, the interfaces of the sample 204 and window 203 are desirably in close contact with each other at least in a measurement range.

If a gap is inevitably generated, data of that irradiation position is eliminated from the obtained result of the complex refractive index distribution.

Also, matching liquid having a complex refractive index close to that of the sample 204 or the window 203 may be previously applied to the front surface of the sample 204. Accordingly, the contactness with respect to the window 203 can be improved. If the sample 204 is a fixed slice, the complex refractive index of the sample 204 can be expected to be around 1.5. Hence, a material having a similar value may be used as the matching liquid. Also, the layer of the matching liquid is required to be sufficiently thin with respect to the wavelength of the terahertz wave, and is desirably one-tenth of the wavelength or smaller. In this specification, even when the matching liquid is applied between the window and the sample, it is defined that the window and the sample contact each other.

Further, a "window 203 only" region, where the front surface is not a mirror surface and the back surface does not contact the sample, is sufficiently provided. Hence, the three regions of the mirror surface 302, the window only region, and the region overlapping the sample 204 are set on the front surface of the window 203. A0 (304), A1 (305), and A2 (306) in FIG. 1 are examples of irradiation spots of the terahertz wave pulses, in the respective regions.

The window 203 is processed in a shape that is easily mounted to and removed from the sample holder 214, and then is provided to the operator. If many samples are present, a plurality of pieces with the same standard (shape, material) are desirably prepared for efficient measurement. In some cases, a window of a material that is different from quartz, which is described above, is suitable depending on the sample. For example, a resin, such as polytetrafluoroethylene that transmits a terahertz wave well and has a lower refractive index than that of quartz, may be used. For any material of the window, the complex refractive index spectrum n~$_w$ in a terahertz band is previously obtained. The data is provided to the operator together with the window, and is stored in the memory unit 216 in the PC 213. The operator properly selects data of a complex refractive index corresponding to a window to be used, and measures a sample. Also, the operator may prepare a window and use the window. In this case, data of a complex refractive index of the window is required to be previously obtained from a document or by preparatory measurement with a transmission system.

Figure 4A:
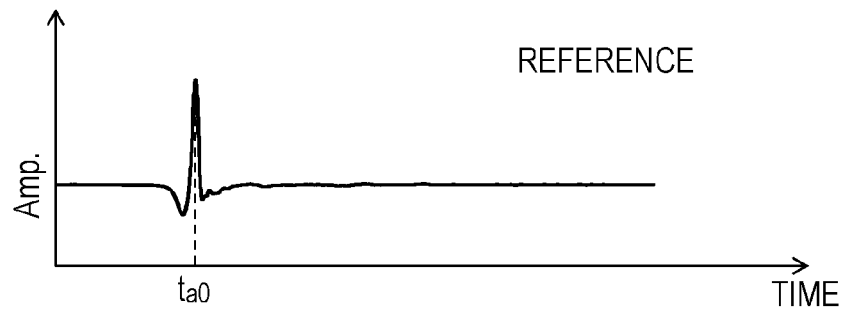
FIG. 4A is an illustration explaining a time waveform of a terahertz wave reflected by a mirror surface according to Example 1.
Figure 4B:
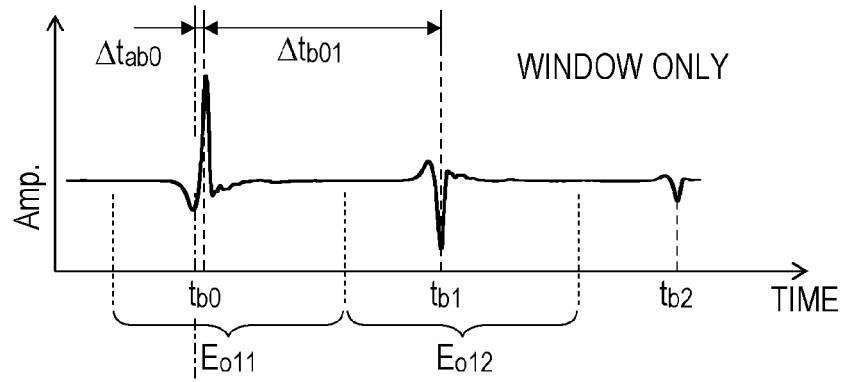
FIG. 4B is an illustration explaining a time waveform of a terahertz wave reflected in a region with only the transmission member according to Example 1.
Figure 4C:
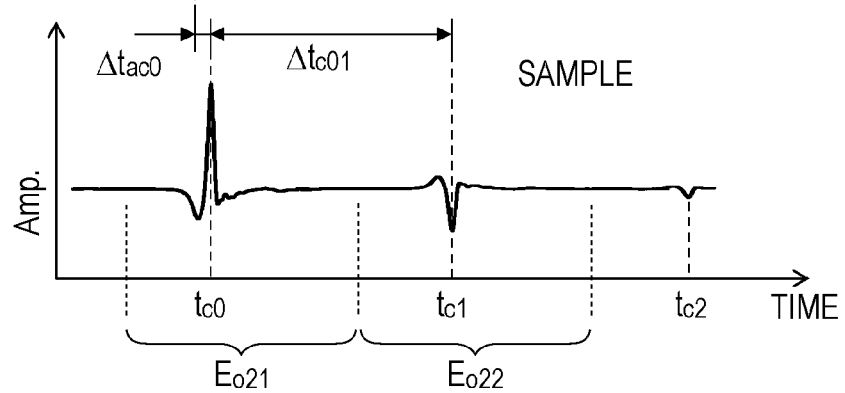
FIG. 4C is an illustration explaining a time waveform of a terahertz wave reflected in a region with the sample arranged according to Example 1.

FIGS. 4A, 4B, and 4C show representative time waveforms obtained when respective irradiation spots are irradiated with terahertz wave pulses. The abscissa axis plots an elapsed time until the waveform of a terahertz wave pulse reaches a detector, and the ordinate axis plots an amplitude of the detected waveform.

FIG. 4A shows a time waveform when an irradiation spot 304 on the mirror surface 302 is irradiated with the terahertz wave pulse, and corresponds to the reflected wave 105 ($E_{oo}$ in FIG. 1. Since the time waveform represents the terahertz wave pulse generated by the photoconductive element well, the time waveform is used as a reference waveform. The time waveform corresponding to the reflected wave 105 was detected at a time $t_{a0}$. There are known various methods of correctly calculating peak positions and intervals. For example, the detail is described in Japanese Patent Laid-Open (Translation of PCT Application) No. 2010-533300. Representative methods include deconvolution, matching a waveform by regression, executing Fourier transform on a peak waveform and then checking a change in time of a phase, etc. A suitable method is selected for each case. In this case, the maximum value in the entire waveform was simply found and the time was set at $t_{a0}$.

FIG. 4B shows a time waveform when the irradiation spot A1 (305) on the surface of only the window 203 is irradiated with the terahertz wave pulse, and corresponds to the reflected wave 109 ($E_{o1}$) in FIG. 1. The maximum amplitude of the reflected wave 107 ($E_{o11}$) at the front surface of the window 203 is detected at a time $t_{b0}$. The minimum amplitude of the reflected wave 108 ($E_{o12}$) at the back surface of the window 203 is detected at a time $t_{b1}$ similarly. With use of a time interval $\Delta t_{b01}$ of both, the thickness $d_{w1}$ of the window 203 at a position near the irradiation spot A1 (305) can be obtained by Expression (2).

Also, a time waveform corresponding to the reflected wave 107 ($E_{o11}$) at the front surface of the window 203 is extracted from the entire waveform of the reflected wave 109 ($E_{o1}$) in FIG. 4B as described below. First, a time interval $\Delta\tau b$, which includes a principal portion of the time waveform corresponding to the reflected wave 107 ($E_{o11}$), and has a pulse interval $\Delta t_{b01}$ or smaller at maximum, is previously determined. Then, for example, it is determined that a time interval of $\Delta\tau b/3$ is set before the time $t_{b0}$ of the maximum amplitude and a time interval $2\Delta\tau b/3$ is set after the time $t_{b0}$ of the maximum amplitude, and then the time waveform corresponding to the reflected wave 107 ($E_{o11}$) is extracted from the entire waveform of the reflected wave 109 ($E_{o1}$). When the time waveform corresponding to the reflected wave 108 ($E_{o12}$) at the back surface of the window 203 is extracted, the extraction is similarly executed such that time intervals are set before and after the time $t_{b1}$ of the minimum amplitude.

FIG. 4C shows a time waveform when the irradiation spot A2 (306) arranged with the sample 204 is irradiated with the terahertz wave pulse. In FIG. 1, the time waveform corresponds to the reflected wave 113 ($E_{o2}$). The reflected wave 112 ($E_{o22}$) reflected by the front surface of the sample 204 (that is the interface with respect to the back surface of the window 203) is detected after the reflected wave 111 ($E_{o21}$) at the front surface of the window 203. Extraction for portions corresponding to both reflected waves and estimation for the thickness $d_{w2}$ of the window at a position near the irradiation spot A2 (306) from a peak interval $\Delta t_{c01}$ of the extracted portions are executed similarly to the previous case in FIG. 4B.

If the front surface of the window 203 is not flat with respect to the sample stage, times at which the reflected waves have the maximum amplitudes at the front surface of the window 203 may vary in the respective time waveforms shown in FIGS. 4A, 4B, and 4C ($\Delta t_{ab0} \approx 0$, $\Delta t_{ac0} \approx 0$). Also, the difference in thickness of the window 203 at the irradiation spots A1 and A2 appears in the time waveforms as a difference in peak interval ($\Delta t_{b01} \neq \Delta t_{c01}$). The peak at a time $t_{b2}$ in FIG. 4B and the peak at a time $t_{c2}$ in FIG. 4C represent pulses each making a round trip again in the window 203. Such pulses are not used in this example, and hence corresponding light rays (waveforms) are omitted in FIG. 1.

Figure 5:
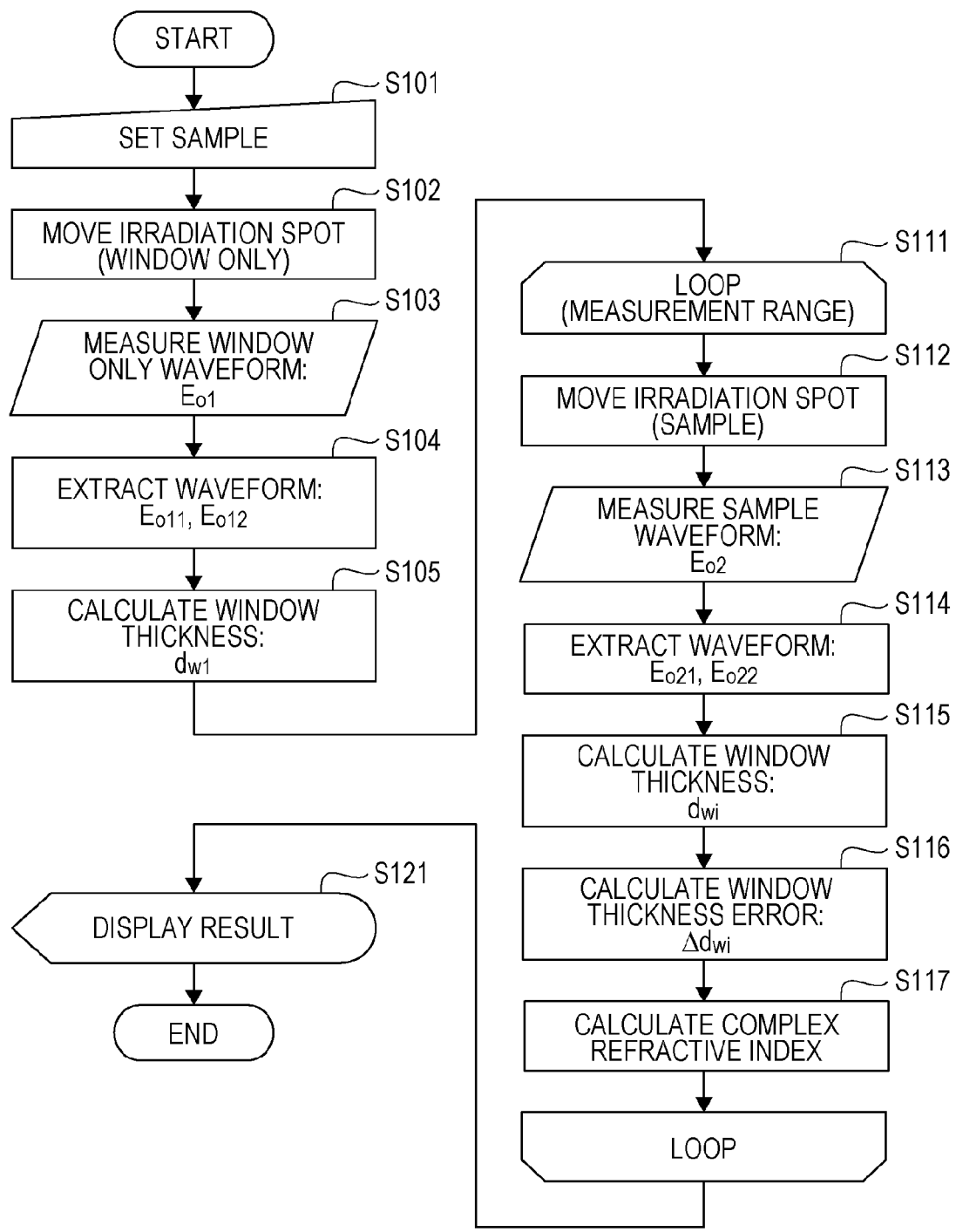
FIG. 5 is a flowchart explaining an example of a measurement procedure according to Example 1.

FIG. 5 shows a basic processing procedure during sample measurement according to this example.

In step S101, the sample 204, which is prepared by the operator, is brought into contact with the window 203 without a gap. Then, the integrated sample 204 and window 203 are set on the sample stage 205.

In step S102 to step S105, measurement relating to the window 203 is executed to obtain reference data. First, in step S102, the control unit 215 moves the sample stage 205 to move the irradiation spot of the terahertz wave pulse to the irradiation spot A1 (305) at a position provided with only the window 203. In step S103, measurement for the window 203 is executed, to obtain the time waveform of the reference wave ($E_{o1}$) serving as the reference which is used later. In step S104, the PC 213 extracts the pulses $E_{o11}$ and $E_{o12}$ reflected by the front surface and the back surface of the window 203, from the time waveform of the reflected wave ($E_{o1}$). Further, in step S105, the PC 213 calculates the thickness $d_{w1}$ of the window 203 at the irradiation position, from the peak interval of both pulses.

In step S111 to step S117, measurement relating to the sample 204 is executed. The steps form a loop that repeats moving the irradiation spot and executing the measurement for a predetermined range. In step S111, the PC 213 increments a counter i of the loop, and determines whether the loop is ended or not. In step S112, the control unit 215 moves the sample stage, to change the irradiation position to a desirable position. In step S113, the sample 204 is irradiated with the terahertz wave pulse through the window 203, to obtain the time waveform of the reflected wave ($E_{o2}$).

The PC 213 mainly executes calculation and display, which are provided later. In step S114, the reflected waves $E_{o21}$ and $E_{o22}$ at the front surface and the back surface of the window 203 are extracted from the time waveform of the reflected wave ($E_{o2}$). Further, in step S115, a thickness $d_{wi}$ of the window 203 at a position near an i-th irradiation spot when counted from the peak interval of both reflected waves is calculated. In step S116, a thickness error of the window 203, that is, a difference $\Delta d_{wi}$ between the thickness $d_{wi}$ of the window 203 at the position near the current irradiation spot and the reference thickness $d_{w1}$ of the window 203 is calculated. In step S117, the complex refractive index $\tilde{n}_s$ of the sample 204 is obtained by using Expression (3) and Expression (6) based on the extracted time waveforms $E_{o11}$, $E_{o12}$, $E_{o21}$, and $E_{o22}$, and the thickness error $\Delta d_{wi}$ of the window.

In this example, the value of the thickness d of the window 203 and the value of the thickness error $\Delta d$ of the window 203 are obtained. However, only the time difference $\Delta t$ of the extracted two waveforms is required to obtain the information of the sample 204 with regard to the difference in thickness of the window 203.

In step S121 after the loop is ended, the real parts of the complex refractive indices obtained for the respective irradiation positions are extracted, and the front surface distribution of the refractive indices is displayed on the PC 213.

FIGS. 6A to 6D show effects of thickness error correction according to this example when refractive index distribution measurement for the sample 204 is actually executed. The sample 204 employed a portion of a subject, in which a living tissue (human large intestine) is formalin-fixed and then paraffin-embedded. The surface was cut in a flat shape by a sharp blade, and was brought into contact with a quartz plate with a thickness of about 1 mm serving as the window 203 while warming the quartz plate. Then, a 10-mm-long and 12-mm-wide region of the sample 204 is measured through the window with an interval of 250 µm, and hence the distribution of refractive indices at the front surface of the sample 204 is obtained.

Figure 6A:
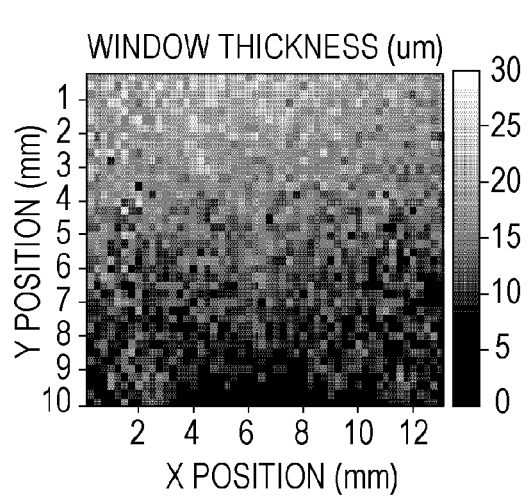
FIG. 6A is a distribution diagram of errors in thickness of the transmission member according to Example 1.
Figure 6B:
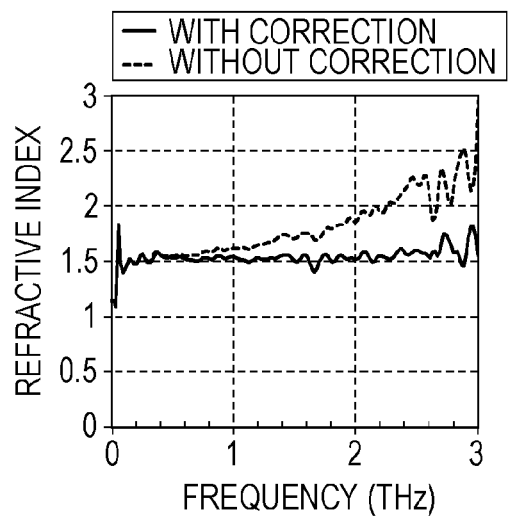
FIG. 6B is a refractive index spectrum acquired in Example 1.

FIG. 6A shows a distribution of thickness errors $\Delta d_w$ of the window 203 obtained in such a case. The differences between the reference thickness $d_{w1}$ obtained in the window-203-only region and the thicknesses $d_{wi}$ of the window 203 obtained at the respective irradiation spots i are provided in the form of a distribution using density variations. Referring to FIG. 6A, it is found that the window 203 used in this example has a difference in thickness of about 30 µm. FIG. 6B shows an example of a refractive index spectrum obtained by measuring a region where the sample 204 is paraffin. The refractive index spectrum calculated with regard to the error caused by the difference in thickness of the window 203 is indicated by a solid line, and the refractive index spectrum calculated based on an assumption that the thickness of the window 203 is $d_{w1}$ in the entire surface is indicated by a dotted line. It is known that the refractive index of the paraffin is almost not frequency dependent, and the refractive index is about 1.5 with any frequency, as the result of another measurement. With the spectra, if the thickness of the window 203 is different at each irradiation position, the refractive index is more deviated from 1.5, which is the original value, as the frequency is higher. It is found that the thickness of the window 203 influences the measurement accuracy.

Figure 6C:
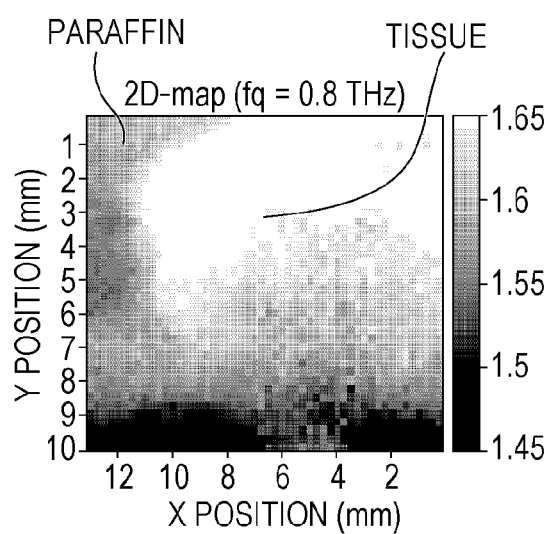
FIG. 6C is a distribution diagram of refractive indices with 0.8 THz before correction for the thickness of the transmission member.
Figure 6D:
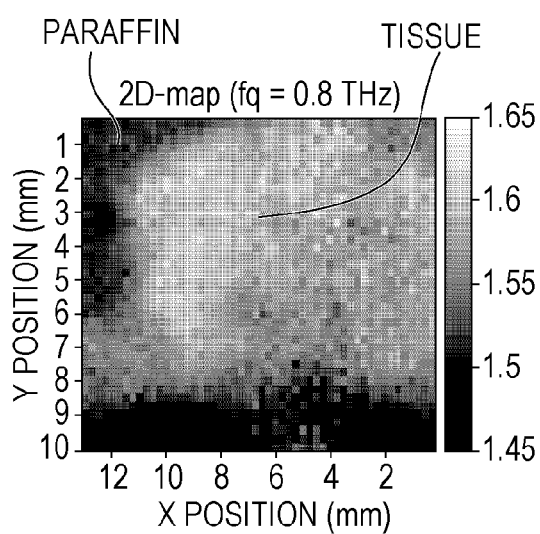
FIG. 6D is a distribution diagram of refractive indices with 0.8 THz after correction for the thickness of the transmission member.

FIGS. 6C and 6D are each a refractive index distribution of the sample 204 at a position near f=0.8 THz, where the intensity of irradiation terahertz wave is maximum. FIG. 6C is a distribution diagram of refractive indices when the thickness error is not corrected. FIG. 6D is a distribution diagram of refractive indices when correction is executed. If the thickness error becomes the order of 10 μm, it is found that the influence on the refractive index value to be calculated is not negligible.

The information acquiring apparatus according to this example can accurately acquire the information of the sample 204 by using the acquired time waveform and the information relating to the thickness of the window 203. To be specific, with reference to the thickness of the window 203 obtained from the reference data of the window 203, correction regarding the difference with respect to the thickness of the window 203 at another irradiation position is individually executed for each irradiation position. Accordingly, the information of the sample 204 can be accurately obtained.

EXAMPLE 2

A configuration of an information acquiring apparatus according to Example 2 is described with reference to FIGS. 12A and 12B. The information acquiring apparatus according this example has a configuration for irradiating a sample with a terahertz wave, the configuration of which is partly different from that of Example 1. However, a method of acquiring information of a sample by using an acquired time waveform is similar to that of Example 1. To be specific, Example 1 provides a configuration that emits a terahertz wave from above. In contrast, this example provides a configuration that irradiates a transmission member or a sample with a terahertz wave from below. Hereinafter, description for part common to Example 1 is omitted, and description is given while focusing on the difference in configuration and action.

Figure 12A:
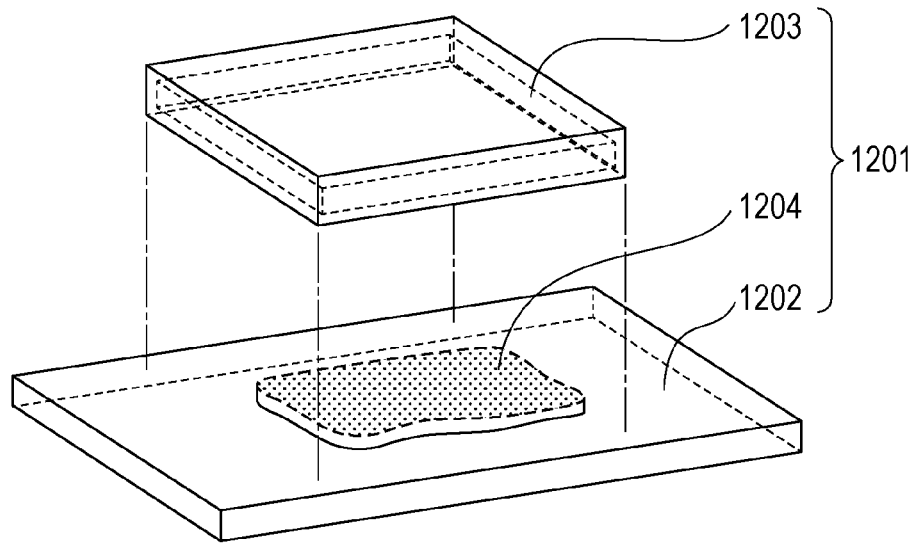
FIG. 12A is an illustration explaining arrangement of a sample and a transmission member according to Example 2.

FIG. 12A shows arrangement of a sample and a transmission member in this example. FIG. 12B shows a configuration of a principal portion of the information acquiring apparatus of this example. As shown in FIG. 12A, in this example, a sample holder 1201, on which a sample is arranged, includes a transmission member (window) 1202 and a cover 1203, which are integrated.

The window 1202 uses a material that transmits a terahertz wave well, and is processed so that the front surface and the back surface of the window 1202 have high flatness and high parallelism. The flatness and parallelism of the front surface and the back surface of the window 1202 may be desirably high, although a correction unit may be employed. If the shape is a substrate-like shape, the flatness may be 1 μm or smaller, and the parallelism may be 10 μm or smaller as target values within a measurement range, although the values may vary depending on the material.

In this example, a member cut from z-cut quartz by a thickness of about 1 mm was used for the window 1202. In a 20×50 mm range relating to measurement, both surfaces each have a flatness of about 5 μm and a parallelism (thickness error) of about 1 μm on the PV-value basis. A substrate being highly flat and parallel is used; however, a slight warp generated by additional processing influences the flatness and parallelism.

A sample 1204 is arranged so that the front surface to be measured contacts the window 1202. In this case, a tissue piece of raw pork has a thickness smaller than 1 mm was prepared as the sample 1204. Since the tissue piece having high moisture content, the contactness between the front surface of the sample 1204 in the form of a thin piece and the window 1202 was good.

The sample 1204 is arranged on the sample holder 1201. To be specific, the sample 1204 is arranged between the cover 1203 being hollow and the window 1202. The cover 1203 has an effect of preventing the sample 1204 from being dried, and an effect of restricting the characteristics of the sample 1204 from being changed during measurement. In addition, the cover 1203 prevents the moisture, which comes out from the sample 1204, from leaking to the information acquiring apparatus.

Figure 12B:
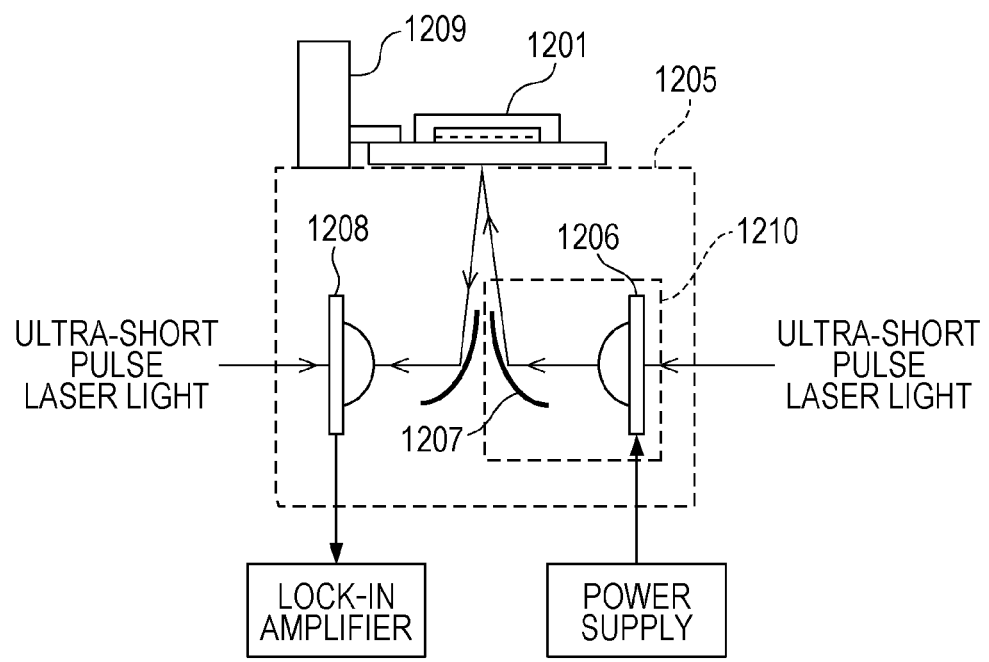
FIG. 12B is an illustration explaining a configuration inside a casing according to Example 2.

FIG. 12B is a cross-sectional view showing a configuration in a casing of the information acquiring apparatus according to this example. The configuration other than the configuration in the casing is common to Example 1, and hence the description is omitted.

During measurement, the inside of a casing 1205 is filled with the dry air etc. Ultra-short pulse laser light is branched by a half mirror into two portions similarly to Example 1, and the branched light portions are guided into the casing 1205 through holes made in the front surface of the casing 1205. One of the two ultra-short pulse laser light portions is emitted on a generation unit 1206 of an irradiation unit 1210, and the other is emitted on a detection unit 1208. Both the generation unit 1206 and the detection unit 1208 of this example are photoconductive elements. The irradiation unit 1210 includes the generation unit 1206 and a parabolic mirror 1207.

A terahertz wave pulse generated from the generation unit 1206 is collected by the parabolic mirror 1207 and propagates to the upper side. The upper surface of the casing 1205 is flat. A hole for sample observation is made in the front surface of the casing 1205. The collected terahertz wave pulse passes through the hole and is emitted on the sample 1204 in the sample holder 1201. To be specific, the terahertz wave pulse passing through the hole for sample observation provided in the front surface of the casing 1205 is emitted on the sample 1204 through the window 1202. The terahertz wave pulse reflected by the sample 1204 is collected by another parabolic mirror, and is detected by the detection unit 1208.

The sample holder 1201 is mounted to an XY stage 1209 so that the back surface of the sample holder 1201 slides on the upper surface of the casing. When a control unit (not shown) properly controls the XY stage 1209, the terahertz wave pulse can be emitted at a desirable position of the sample 1204.

Figure 13A:
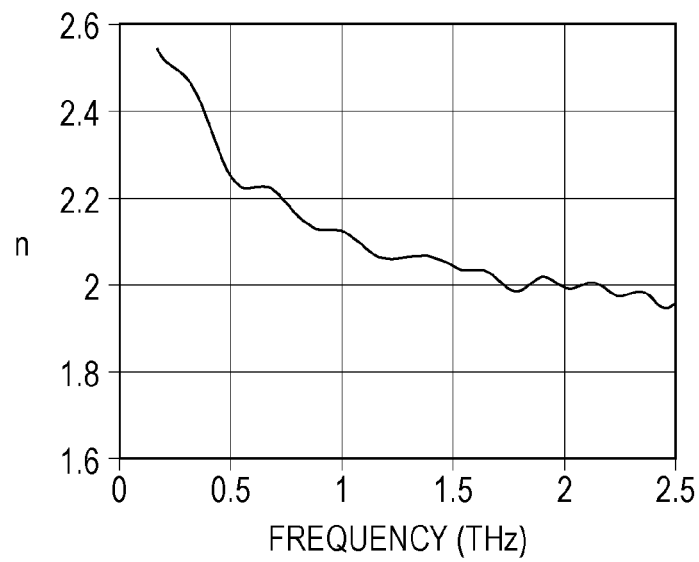
FIG. 13A is a refractive index spectrum acquired in Example 2.
Figure 13B:
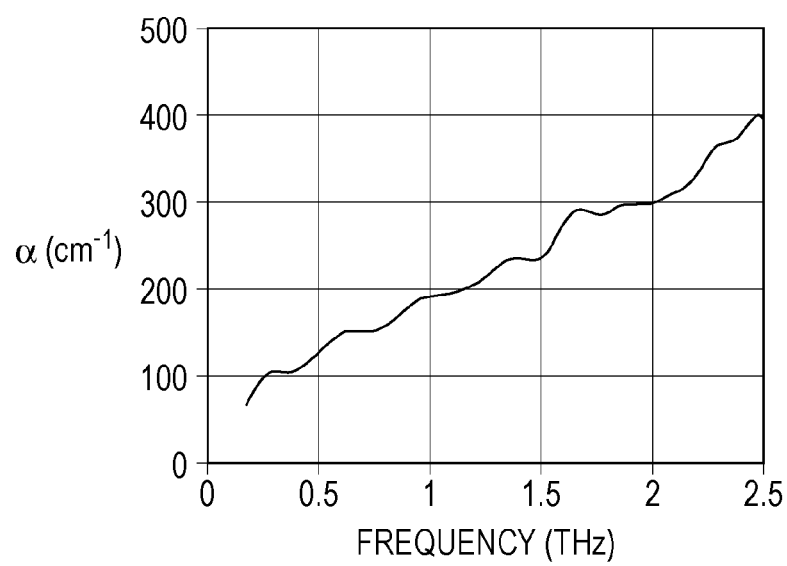
FIG. 13B is an absorption coefficient spectrum acquired in Example 2.

With the information acquiring apparatus of this example, the sample 1204 was measured, and information of the sample 1204 was acquired by using a time waveform acquired similarly to Example 1 and information relating to the thickness of the window 1202. In this case, FIG. 13A shows a refractive index spectrum in a terahertz-wave band as the information of the sample 1204. Also, FIG. 13B shows an absorption coefficient alpha ($cm^{-1}$) spectrum in a terahertz-wave band.

The refractive index spectrum in FIG. 13A tends to be high at the low frequency side. The absorption coefficient spectrum in FIG. 13B tends to be high at the high frequency side. These tendencies are similar to those of water, and represent that the sample 1204 has a relatively high moisture content. That is, even if the information acquiring apparatus of this example executes measurement with use of a terahertz wave, the information of the sample 1204 can be highly accurately acquired by using the acquired time waveform and the information relating to the thickness of the window 1202 when the information of the sample 1204 is obtained.

Each spectrum is also similar to the measurement result acquired by measuring a fresh slice of an organ of a rat with a terahertz wave, described in S. Y. Huang et al., Physics in Medicine and Biology, (2009), 54, 149-160. Also, each spectrum is similar to the result described in other document in which a living body tissue is measured. Even when a living body tissue is used as a sample, information which represents the characteristics of the sample may be acquired.

Also, the information acquiring apparatus of this example has a good reproducibility of an irradiation position of a terahertz wave pulse with respect to the sample 1204. This is mainly because of the configuration of the apparatus. The front surface of a sample is aligned to the upper surface of the casing and is irradiated with a terahertz wave pulse. More specifically, excellent stabilities of the height position of the front surface of the sample 1204 which contacts the window 1202 and the incident angles of a terahertz wave pulse to the window 1202 and the front surface of the sample 1204 contribute to the reproducibility.

EXAMPLE 3

Figure 7:
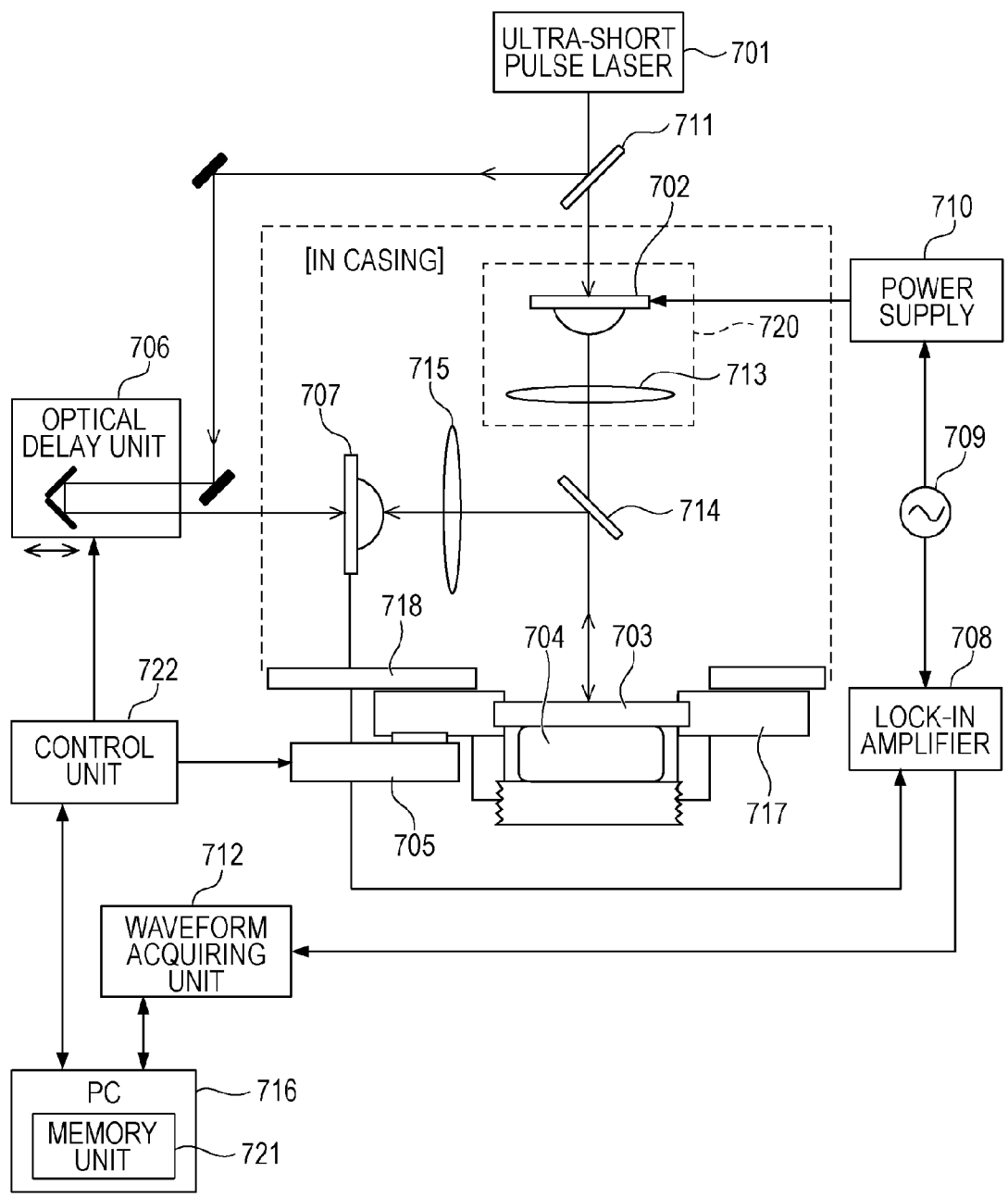
FIG. 7 is an illustration explaining a configuration of an information acquiring apparatus according to Example 3.

Example 3 is described with reference to FIG. 7. In Example 1, the terahertz wave pulses are emitted on the window 203 and the sample 204 obliquely. In this example, terahertz wave pulses are emitted on a window 703, serving as a transmission member, and a sample 704 perpendicularly. Hereinafter, description of a common portion is omitted as possible, and description is given while focusing on the difference in configuration and action.

In this example, the terahertz wave pulse generated by a photoconductive element 702, serving as a generation unit, is collected by a lens 713. Then, the terahertz wave pulse passes a half mirror 714, and is emitted on the sample 704 through the window 703 perpendicularly. The lens 713 uses, for example, a lens formed by processing a resin or a single crystal silicon (Si) that transmits a terahertz wave well. The terahertz wave pulse reflected by the window 703 or the sample 704 is returned in the opposite direction along the same axis as that of the incident wave, and is branched by the half mirror 714. The branched terahertz wave pulse is collected by another lens 715, and then is incident on the front surface of a photoconductive element serving as a detection unit 707.

Similarly to Example 1, the optical system of the terahertz wave pulse is stored in a casing filled with the dry air etc. In this example, an observation hole is provided in a portion of the casing. The observation hole causes the terahertz wave pulse to pass therethrough. A sample holder 717 that holds the window 703 and the sample 704 contacts a surface 718 surrounding the observation hole so that the window 703 faces the observation hole. Thus, the casing is closed. The surface 718 and the sample holder 717 may not contact each other, and the casing is desirable if the casing is hermetically sealed. The sample holder 717 is mounted to a sample stage 705. When a control unit 722 controls the sample stage 705, the sample stage 705 and the sample holder 717 are moved and slide together with respect to the casing. In this example, the irradiation position of the sample 704 is changed as described above.

The detection result of the detection unit 707 is sent to a waveform acquiring unit 712 through a lock-in amplifier 708. The waveform acquiring unit 712 acquires the time waveform of the terahertz wave pulse. The information of the sample 704 is acquired by using the time waveform acquired as described above and the information relating to the thickness of the window 703, by a method similar to the above-described example. At this time, reference data stored in a memory unit 721 of a PC 716 is also used.

The information of the sample 704 obtained by the information acquiring apparatus according to this example is displayed on a display (not shown) of, for example, the PC 716, in the form of frequency spectrum or surface distribution. With the configuration of this example, when the information of the sample 704 is obtained, by using the information relating to the thickness of the window 703 at the irradiation position of the terahertz wave, measurement accuracy is increased. Also, advantages of this example are that the optical system of the terahertz wave can be reduced in size, and the terahertz wave is incident perpendicularly ($\theta_i=0$ in FIG. 1). Since the optical system is reduced in size, the size of the entire apparatus can be reduced. Accordingly, portability is increased. Also, the configuration in which the terahertz wave is incident perpendicularly on the sample 704 makes a contribution to an increase in accuracy of the information of the sample 704 to be calculated.

In this example, the optical axes are aligned because of the perpendicularly incident configuration. Hence, when the terahertz wave is incident obliquely, the reflected wave from the front surface of the window and the reflected wave from the back surface of the window are collected at slightly different positions on the photoconductive element 707. In contrast, in this example, the influence of such a positional deviation can be decreased. Of course, Example 1 provides measurement accuracy that is sufficient in practical use. However, with this example, the measurement accuracy can be further increased.

EXAMPLE 4

In each of the above-described three examples, a difference in thickness of the window (transmission member) is obtained at each irradiation position to correct an error of the thickness of the window. In this example, a smooth imaginary thickness distribution is obtained on the basis of thicknesses of the window at a plurality of irradiation positions. This imaginary thickness distribution may be obtained by leveling off errors of about several micrometers generated by measurement and estimation for a peak position.

As described above, the plate-shaped transmission member, which is commercially available, can be approximated to a member in which smooth planes face each other with a very small inclination. Hence, the thickness of the transmission member may follow the aforementioned imaginary thickness distribution. In the following refractive index estimation, an error generated because of the thickness of the transmission member is collected by using the imaginary thickness distribution.

Figure 8:
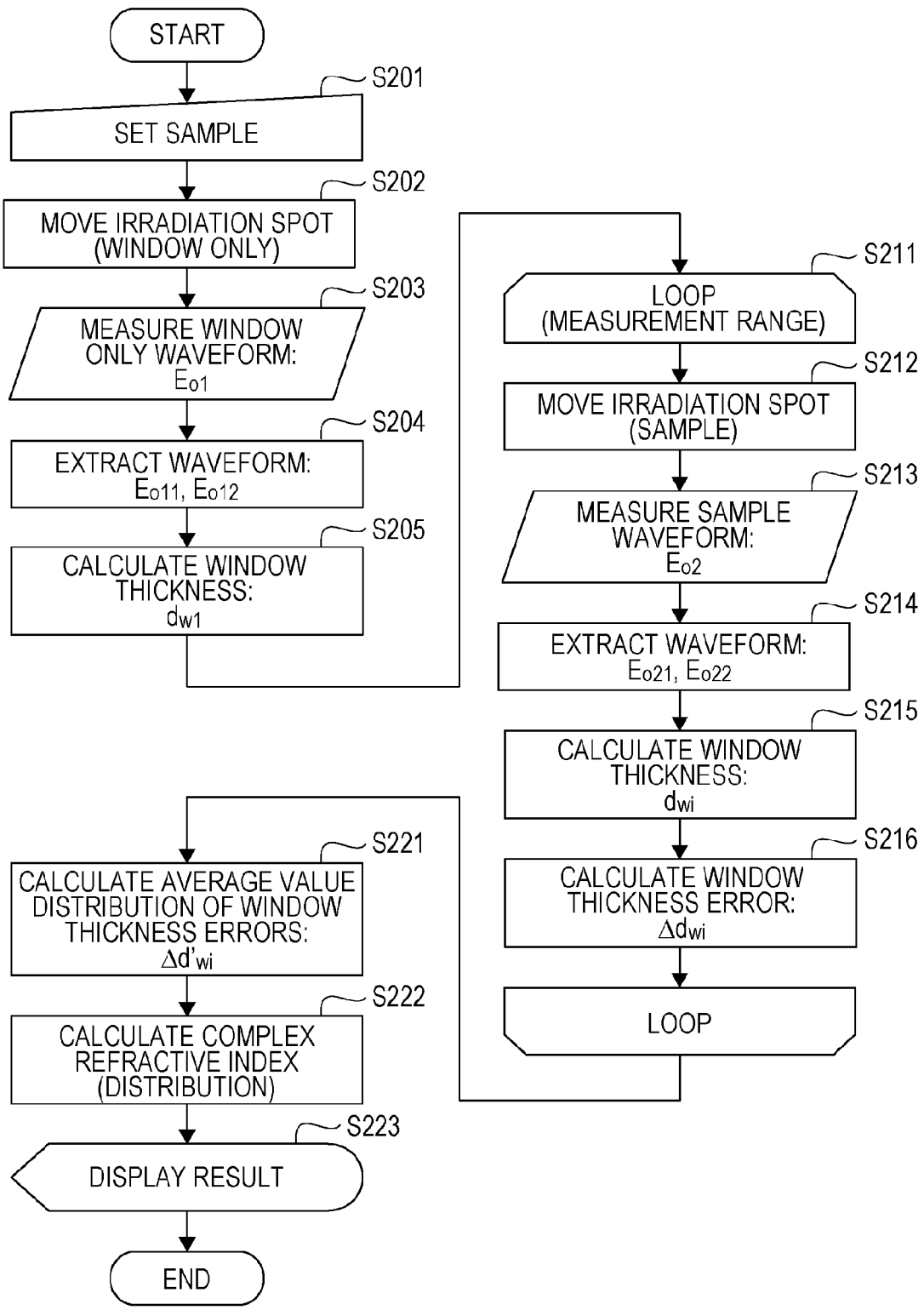
FIG. 8 is a flowchart explaining a measurement procedure according to Example 4.

FIG. 8 shows a processing procedure for sample measurement according to this example. A major part of the processing procedure is common to the processing procedure of the former example (FIG. 5). The difference is processing after a series of region measurement (loop) is ended. In the former example, the PC 213 obtains a reflectivity etc. in step S117 immediately after the PC 213 obtains the difference $\Delta d_{wi}$ from the reference of the thickness of the window, which is the transmission member, in step S116. In contrast, in this example, in step S221 after the loop (step S211 to step S216), the PC 213 analyzes a distribution of differences $\Delta d_{wi}$ in thickness of the transmission member, and calculates an imaginary plane, which is an averaged error distribution. In step S222, the PC 213 obtains a refractive index by using an error $\Delta d'_{wi}$ of the transmission member on the imaginary plane. The obtained refractive index is displayed on the PC 716 in the form of front surface distribution or frequency spectrum (S223).

Figure 9:
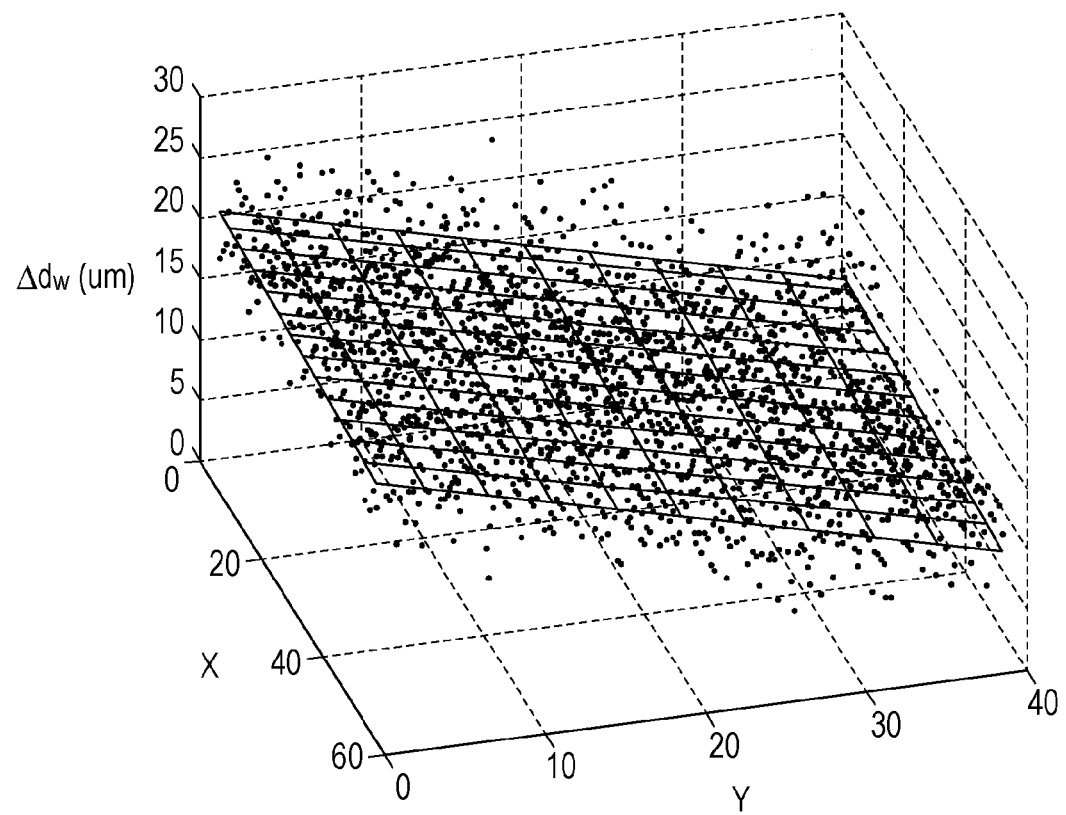
FIG. 9 is an illustration explaining a distribution and averaging of errors in window thickness during measurement.

FIG. 9 shows actually measured values of errors in thickness of the transmission member (black dots) and an imaginary plane obtained by analyzing the distribution of the actually measured values (plane formed by straight lines). The X axis and Y axis plot steps of the irradiation spots (each interval being 250 µm), and the Z axis plots the error $\Delta d_w$ of the thickness $d_{wi}$ of the transmission member with respect to the reference value $d_{w1}$, obtained from the first and second peak interval at each irradiation spot.

The actually measured value is decreased as the value along the Y axis is increased. This suggests that the thickness of the used transmission member is gradually decreased in the Y direction. Values of $\Delta d_w$ at adjacent irradiation spots may differ from each other in a range from several micrometers to about 10 µm. Major factors of this difference may be a noise during measurement and an error when a peak position is obtained. In fact, the front surface of the transmission member evaluated by other method such as using a surface roughness tester is the order of micrometer or smaller except inclination.

An imaginary plane that approximates the distribution of actually measured values best is obtained by executing principal component analysis for the actually measured values. Principal component analysis is executed on data of a measurement point i ($x_i$, $y_i$, $\Delta d_{wi}$) in a sample region, and a plane formed by obtained characteristic vectors of first and second principal components is an imaginary plane. The height of the imaginary plane at each irradiation position ($x_i$, $y_i$) may be used as an estimated value $\Delta d'_{wi}$ of a difference in thickness of the transmission member.

With this example, the difference in thickness of the transmission member with the influence of a noise etc. reduced can be obtained. Accordingly, the accuracy of the complex refractive index to be calculated can be increased.

The method of obtaining a thickness error of the transmission member with reference to the information at each measurement point is described above. As another easier method, an imaginary plane for differences in thickness of the transmission member may be created from the result when three or more positions are measured in the region only provided with the transmission member. As shown in FIG. 3A, the region extending outside the measurement region and only provided with the transmission member may be used. The irradiation position ($x_i$, $y_i$) is previously determined, a measurement point ($x_i$, $y_i$, $\Delta d_{wi}$) is obtained by adding a measured thickness error $\Delta d_{wi}$ of the transmission member to the predetermined irradiation spot, and the imaginary plane is obtained from the measurement point. With the configuration of this example, when the information of the sample 704 is obtained, by using the information relating to the thickness of the transmission member at the irradiation position of the terahertz wave, measurement accuracy is increased.

This method provides advantages that the calculation is easy and that the calculation is hardly influenced by a disorder of the interface in the measurement region. If the contactness between the back surface of the transmission member and the front surface of the sample is bad and many air bubbles are contained, a situation, in which the thickness error of the transmission member obtained at each measurement point is deviated from the original value, may be increased. In this case, a good result is obtained if the imaginary plane is obtained only by using the information of the thickness obtained from the region with only the transmission member. The information of the sample obtained by the information acquiring apparatus according to this example is displayed on a display (not shown) of, for example, a PC, in the form of frequency spectrum or front surface distribution.

EXAMPLE 5

Example 5 is described. In any of above-described Example 1 to Example 4, during a series of measurement, measurement is executed at a desirable position in the region with only the transmission member, and the information of the sample is acquired with reference to the acquired information. In this example, data relating to a substance to be used as a transmission member is previously stored, and is used as reference data when a window having approximately equal complex refractive index is used. Hereinafter, description of a common portion is omitted as possible, and description is given while focusing on the difference in configuration and action.

The configuration of the information acquiring apparatus according to this example is similar to that of Example 1. The difference is that data for the window 203 (reference data) is previously stored in the memory unit 216 of the PC 213 in FIG. 2. The data for the window 203 (reference data) may be, for example, a time waveform acquired by measuring the window 203 by using the information acquiring apparatus of this example, or information relating to the thickness of the window 203 obtained by the time waveform and a frequency spectrum. Alternatively, the information may not be acquired from the memory unit 216 of the PC 213. A method of acquiring information stored in other external memory, such as a SD card, connected to the PC 716, or a method of acquiring information through a network may be used.

Figure 10:
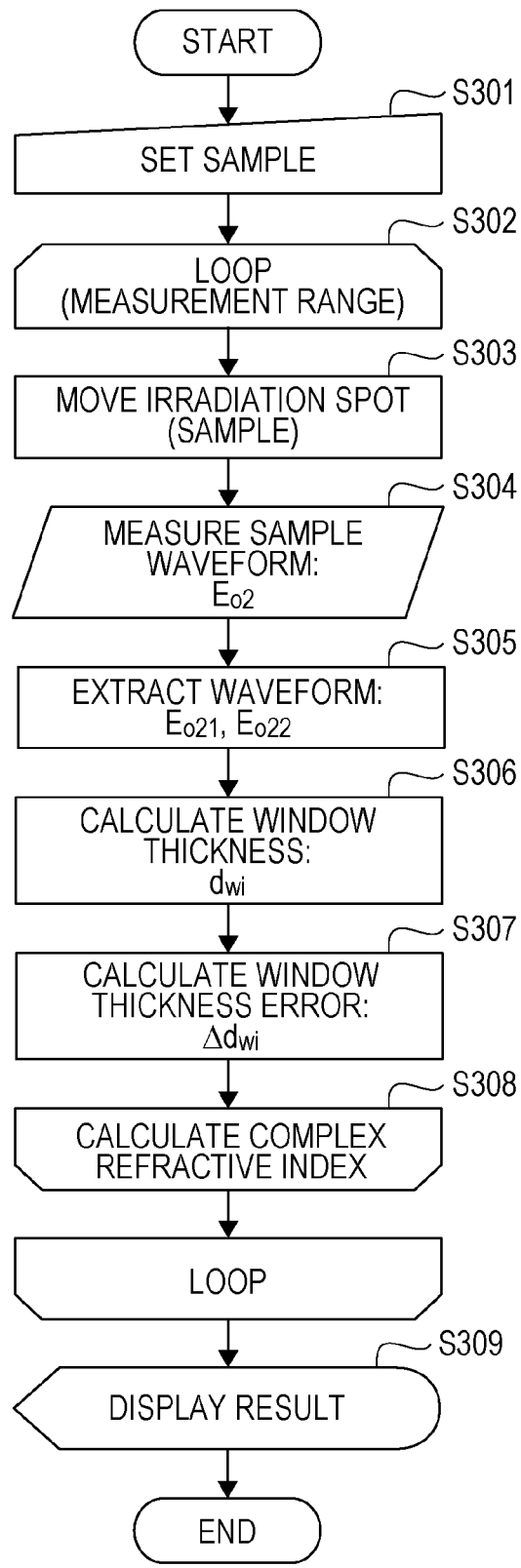
FIG. 10 is a flowchart explaining a measurement procedure according to Example 5.

A measurement procedure in this example is described with reference to FIG. 10.

In step S301, the integrated sample 204 and window 203 are set on the sample stage 205. In this example, a sample with the configuration shown in FIGS. 3A and 3B is used.

Processing from step S302 to step S308 relate to measurement of the sample 204. The steps form a loop that repeats moving the irradiation spot and executing the measurement for a predetermined range. In step S302, the PC 213 increments a counter i of the loop, and determines whether the loop is ended or not. In step S303, the control unit 215 moves the sample stage 205, to change the irradiation position to a desirable position. In step S304, the sample 204 is irradiated with the terahertz wave pulse through the window 203, and the detection unit 207 detects the reflected wave ($E_{o2}$) and acquires the time waveform.

The PC 213 mainly executes calculation and display, which are provided later. In step S305, the pulses $E_{o21}$ and $E_{o22}$ reflected by the front surface and the back surface of the window 203 are extracted from the time waveform 113 of the reflected wave ($E_{o2}$). Further, in step S306, a thickness $d_{wi}$ of the window 203 at a position near an i-th irradiation spot when counted from the peak interval of both reflected pulses is calculated.

In step S307, a thickness error of the window 203, that is, a difference $\Delta d_{wi}$ between the thickness $d_{wi}$ of the window 203 at the position near the current irradiation spot and the reference thickness $d_{w1}$ of the window 203 is calculated. At this time, the thickness $d_{w1}$ of the window 203 serving as the reference is acquired from the reference data stored in the PC 213. In step S308, "the pulse waveforms $E_{o21}$ and $E_{o22}$ extracted in step S305," "pulse waveforms $E_{o11}$ and $E_{o12}$ obtained from the reference data stored in the PC 213," and "the thickness error $\Delta d_{wi}$ of the window 203 obtained in step S1007" are used. To be specific, the complex refractive index $\tilde{n}_s$ of the sample 204 is calculated by using the pulse waveforms $E_{o21}$, $E_{o22}$, $E_{o11}$, and $E_{o12}$, and the thickness error $\Delta d_{wi}$ of the window 203 through Expression (3) and Expression (6).

With the configuration of this example, when the information of the sample 204 is obtained, by using the information relating to the thickness of the window 203 at the irradiation position of the terahertz wave, measurement accuracy is increased. Also, in the above-described example, as shown in FIG. 2, the thickness of the window 203 is obtained by executing measurement of the region with only the window 203. However, the step can be omitted in this example. Instead of the step, the reference data stored in the memory of the PC 213 etc. is used to obtain the information of the sample 204 with regard to the thickness error of the window 203. Also, the method of using the previously stored reference data like this example may be applied to above-described Example 3 or Example 4.

In this example, the step of acquiring the information relating to the reference position can be omitted, and hence the time required for measurement can be reduced.

EXAMPLE 6

Example 6 is described with reference to the drawing.

In any of the above-described examples, the sample stage to which the window and the sample are fixed serves as a position change unit. When the irradiation position of the terahertz wave is changed, the sample stage is controlled to move the sample and the window. In this example, the sample is not moved, but the terahertz wave is moved to change the position of the irradiation spot and to execute distribution measurement.

Figure 11:
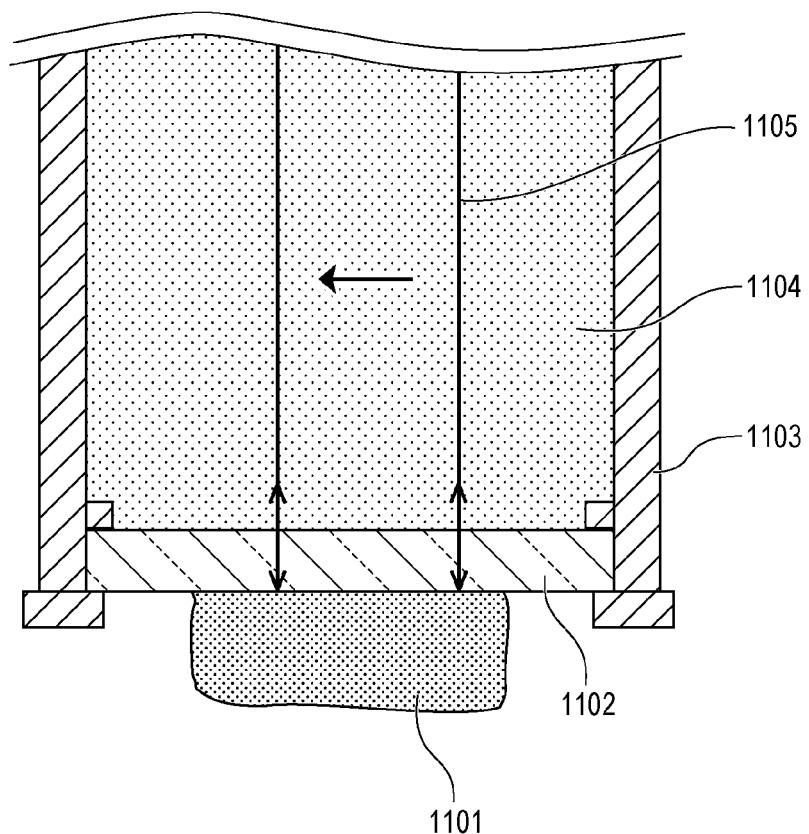
FIG. 11 is an illustration explaining an information acquiring apparatus according to Example 6.

FIG. 11 is a cross-sectional view of a principal portion of this example.

A probe 1103 is a portion of an information acquiring apparatus using terahertz time-domain spectroscopy of a reflection system, in which portability of a portion that contacts a sample 1101 is increased for easier measurement. A path of a terahertz wave pulse 1105 is provided in a casing. Water vapor is eliminated from an atmosphere 1104 in the casing as much as possible. A window 1102 is a plate-shaped transmission member that transmits a terahertz wave well and is flat. The window 1102 is mounted to the casing of the probe 1103 and separates the atmosphere 1104 in the casing from the outside air.

When the sample 1101 is measured, the window 1102 is pressed to the front surface of the sample 1101, so that the front surface of the sample 1101 becomes flat. A terahertz wave pulse is generated from a light source (not shown), is collected, then is guided in the casing, and is emitted on the sample 1101 through the window 1102. The reflected wave reflected by the front surface of the window 1102 or the sample 1101 is returned in the casing, and the time waveform of the wave is measured by a detection unit (not shown). The irradiation position of the terahertz wave pulse on the sample 1101 is changed by changing the position of the terahertz wave pulse 1105. The configuration for scanning is provided at a deep side of the probe 1103 although it is not shown.

The window 1102 may be mounted to and removed from the probe 1103, and hence may be exchanged, to prevent any of various samples 1101 from being influenced by a scuff or contamination on the front surface. For measurement, data of a complex refractive index is required to be properly selected in accordance with the material of the window 1102, as described above.

With the configuration of this example, the sample 1101 is not required to be arranged at the sample holder during measurement. The probe may be brought close to the sample 1101 and the window 1102 may be brought into contact with the surface to be measured of the sample 1101. Accordingly, selectivity of the sample 1101 can be increased. For example, the configuration is suitable if skin of an animal or a human, or a tissue of the surface of a viscus in case of an endoscope in a living state (in-vivo). With the configuration of this example, information of the sample 1101 can be acquired by a method similar to the method of any of the above-described examples. When the information of the sample 1101 is acquired, by using the information relating to the thickness of the window 1102 at the irradiation position of the terahertz wave, measurement accuracy is increased.

EXAMPLE 7

Example 7 is described. In any of the above-described examples, the thickness of the transmission member and the plane distribution are obtained from the reflected waveform of the terahertz wave pulse. In this example, the thickness of the transmission member is obtained by using light with a shorter wavelength.

To be specific, if the transmission member is transparent to the terahertz wave, the thickness of the transmission member is acquired by using an optical measurement apparatus using visible light or infrared light. For example, when a displacement meter based on triangulation that detects a very small change in reflection angle at the front surface is used, the front surface position and the thickness of the transmission member can be obtained with accuracy of 100 nm or smaller.

The thickness of the transmission member at the irradiation position is measured by the displacement meter before or after the sample measurement with the terahertz wave or more preferably, at the same time as the sample measurement. The thickness of the transmission member is used for acquiring the information of the sample. The thickness of the transmission member may be previously measured over the entire surface, and the thickness may be associated with the measurement result with the terahertz wave. Alternatively, a thickness distribution of the transmission member may be estimated from the thicknesses at three or more positions as described in Example 4.

With the configuration of this example, the thickness of the transmission member at the irradiation spot can be further accurately obtained.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

For example, in the above-described examples, the front surface distribution of a property is measured by executing measurement at a plurality of positions. However, the embodiment may be applied even if measurement is executed at a single point of a sample. In this case, even if the thickness of the window when the reference data is acquired is different from the thickness of the transmission member at the irradiation position of the sample, highly accurate measurement can be executed. Also, even when measurement is executed for only a single point of each of a plurality of samples contacting the transmission member, the embodiment may be applied. At this time, the thicknesses of the respective transmission members, including the transmission member for acquiring the reference data, are desirably equivalent to each other. However, even if the thicknesses are different, measurement can be executed with high accuracy by application of the embodiment.

The thickness of the transmission member may be measured by a mechanical method by using, for example, a profile measuring apparatus, other than an optical measurement method using the terahertz wave (described in the examples) or light with a wavelength shorter than the wavelength of the terahertz wave.

With the information acquiring apparatus according to any of the above-described embodiment and examples, when the information of the sample is obtained, by using the information relating to the thickness of the window at the irradiation position of the terahertz wave, measurement accuracy can be increased.

This application claims the benefit of Japanese Patent Application No. 2013-073649 filed Mar. 29, 2013 and No. 2014-035844 filed Feb. 26, 2014, which are hereby incorporated by reference herein in their entirety.

What is claimed is:

1. An information acquiring apparatus that acquires information of a sample, comprising:
   an irradiation unit configured to irradiate an irradiation position of the sample with a terahertz wave through a transmission member being in contact with the sample;
   a detection unit configured to detect a terahertz wave reflected by the transmission member and a terahertz wave reflected by the sample;
   a waveform acquiring unit configured to acquire a time waveform of the terahertz wave reflected by the transmission member and a time waveform of the terahertz wave reflected by the sample, by using detection results of the detection unit; and
   an information acquiring unit configured to acquire the information of the sample by using the time waveform of the terahertz wave reflected by the transmission member, the time waveform of the terahertz wave reflected by the sample, and information relating to a thickness of the transmission member at the irradiation position.

2. The information acquiring apparatus according to claim 1, wherein the information acquiring unit acquires the information of the sample by additionally using reference data obtained by irradiating the transmission member or a substance, which has a refractive index approximately equal to a refractive index of the transmission member, with a terahertz wave and acquiring a time waveform of a terahertz wave reflected by a front surface of the transmission member or the substance and a time waveform of a terahertz wave reflected by a back surface of the transmission member or the substance.

3. The information acquiring apparatus according to claim 2, wherein the reference data is data obtained by irradiating a region, where the transmission member does not contact the sample, with a terahertz wave and acquiring a time waveform of a terahertz wave reflected by a front surface of the transmission member and a time waveform of a terahertz wave reflected by a back surface of the transmission member.

4. The information acquiring apparatus according to claim 2, wherein the reference data is data obtained by acquiring a time waveform of the terahertz wave reflected by the front surface of the transmission member or the substance before the transmission member is brought into contact with the sample and a time waveform of the terahertz wave reflected by the back surface of the transmission member or the substance before the transmission member is brought into contact with the sample.

5. The information acquiring apparatus according to claim 2, wherein the information acquiring unit acquires the information of the sample by using a difference between the thickness of the transmission member at the irradiation position and a thickness of the transmission member acquired by using the reference data, as the information relating to the thickness of the transmission member at the irradiation position.

6. The information acquiring apparatus according to claim 2, wherein the information acquiring unit acquires the information of the sample by using a phase difference generated between the terahertz wave reflected by the transmission member and the terahertz wave reflected by the sample, as the information relating to the thickness of the transmission member at the irradiation position.

7. The information acquiring apparatus according to claim 2, wherein the reference data is data including at least one of the time waveform of the terahertz wave reflected by the front surface of the transmission member or the substance and the time waveform of the terahertz wave reflected by the back surface of the transmission member or the substance, a frequency spectrum acquired by using the time waveforms, and a thickness of the transmission member or the substance.

8. The information acquiring apparatus according to claim 2, further comprising a memory unit configured to store the reference data.

9. The information acquiring apparatus according to claim 1, wherein the terahertz wave reflected by the transmission member is a terahertz wave reflected by a front surface of the transmission member.

10. The information acquiring apparatus according to claim 1, wherein the information acquiring unit acquires the information relating to the thickness of the transmission member at the irradiation position by using the time waveform of the terahertz wave reflected by the transmission member and the time waveform of the terahertz wave reflected by the sample.

11. The information acquiring apparatus according to claim 1, further comprising:
   a position change unit configured to change the irradiation position of the terahertz wave,
      wherein the information acquiring unit acquires the information of the sample by using the information relating to the thickness of the transmission member at the irradiation position for each irradiation position changed by the position change unit.

12. The information acquiring apparatus according to claim 1, wherein the thickness of the transmission member is not uniform.

13. The information acquiring apparatus according to claim 1, wherein the information acquiring unit acquires the information of the sample by using the information relating to the thickness of the transmission member at the irradiation position and correcting an error, which is generated because the thickness of the transmission member is not uniform.

14. The information acquiring apparatus according to claim 1, wherein the terahertz wave is a pulsed wave.

15. The information acquiring apparatus according to claim 1, wherein the transmission member has a known refractive index.

16. The information acquiring apparatus according to claim 1,
wherein the irradiation unit includes a generation unit configured to generate a terahertz wave, and
wherein the information acquiring apparatus further comprises an adjustment unit configured to adjust a time point at which the generation unit generates a terahertz wave or the detection unit detects a terahertz wave.

17. The information acquiring apparatus according to claim 1, wherein the information acquiring unit acquires information of a property or a shape of the sample by using a difference between a time, at which the time waveform of the terahertz wave reflected by the transmission member is detected, and a time, at which the time waveform of the terahertz wave reflected by the sample is detected, as the information relating to the thickness of the transmission member at the irradiation position.

18. The information acquiring apparatus according to claim 1, wherein the information acquiring unit acquires a complex refractive index of the sample.

19. An information acquiring method of acquiring information of a sample, comprising:

irradiating an irradiation position of the sample with a terahertz wave through a transmission member being in contact with the sample;

detecting a terahertz wave reflected by the transmission member and a terahertz wave reflected by the sample to provide detection results;

acquiring a time waveform of the terahertz wave reflected by the transmission member and a time waveform of the terahertz wave reflected by the sample, which are acquired by using the detection results; and acquiring the information of the sample by using the time waveform of the terahertz wave reflected by the transmission member and the time waveform of the terahertz wave reflected by the sample, which are acquired by using the detection results, and information relating to a thickness of the transmission member at the irradiation position.

* * * * *